United States Patent [19]
Goldstein et al.

[11] Patent Number: 6,162,167
[45] Date of Patent: Dec. 19, 2000

[54] BLOOD PUMP DEVICE HAVING A JOURNAL

[75] Inventors: Andrew H. Goldstein, Branford, Conn.; John J. Pacella; Dennis R. Trumble, both of Pittsburgh, Pa.; Richard E. Clark, Sewickley, Pa.; Fred W. Moeller, McKeesport, Pa.; George J. Magovern, Pittsburgh, Pa.

[73] Assignee: Allegheny-Singer Research Institute, Pittsburgh, Pa.

[21] Appl. No.: 08/898,584

[22] Filed: Jul. 21, 1997

Related U.S. Application Data

[62] Division of application No. 08/618,084, Mar. 18, 1996, Pat. No. 5,711,753, which is a continuation of application No. 08/228,433, Apr. 15, 1994, abandoned.

[51] Int. Cl.[7] ..................................................... A61M 1/12

[52] U.S. Cl. ............................................................ 600/16

[58] Field of Search .......................................... 600/16, 17

[56] References Cited

U.S. PATENT DOCUMENTS

| 5,118,264 | 6/1992 | Smith ........................................ 600/16 |
| 5,385,581 | 1/1995 | Bramm et al. ............................. 600/16 |
| 5,399,145 | 3/1995 | Ito et al. .................................... 600/16 |

*Primary Examiner*—William E. Kamm
*Attorney, Agent, or Firm*—Ansel M. Schwartz

[57] ABSTRACT

A blood pump device which includes a blood pump having blood transport ports and cannulae connected to the ports. The blood pump device also includes a coating material covering the junction between the inner surfaces of the ports and cannulae. A method of producing a smooth coating. A blood pump device including a second portion having a stator mechanism and a rotor mechanism disposed adjacent to and driven by the stator mechanism. The second portion has a journal disposed about the rotor mechanism to provide support therewith. The second portion has an impeller disposed in the chamber and a seal member for sealing about a shaft of the impeller. The seal member is fixedly attached to the journal so that the seal member is supported by the journal. A mechanism for providing power to the blood pump so that blood can be pumped through a cannula.

14 Claims, 16 Drawing Sheets

BLOOD PUMP DEVICE HAVING A JOURNAL

This is a divisional application of Ser. No. 08/618,084 filed Mar. 18, 1996, now U.S. Pat. No. 5,711,753, which is a continuation application of Ser. No. 08/228,433 filed Apr. 15, 1994, abandoned.

FIELD OF THE INVENTION

The present invention is related in general to medical devices. More specifically, the present invention is related to a blood pump device for cardiac assist.

BACKGROUND OF THE INVENTION

Ventricular assist devices are receiving ever-increasing attention in our society where 400,000 Americans are diagnosed with congestive heart failure each year (Rutan, P. M., Galvin, E. A.: Adult and pediatric ventricular heart failure, in Quall, S. H. (ed), *Cardiac Mechanical Assistance Beyond Balloon Pumping*, St. Louis, Mosby, 1993, pp. 3–24). As a result, collaborative efforts among health care professionals have focussed on the development of various systems to assist the failing heart. These comprise both extracorporeal and implantable pulsatile ventricular assist devices (VAD), as well as non-pulsatile assist pumps.

Extracorporeal systems include the Pierce-Donachy VAD and the Abiomed BVS-5000 VAD. The Pierce-Donachy VAD is positioned on the patient's abdomen and propels blood by means of a pneumatically actuated diaphragm. Its use as a bridge to transplant is well-documented (Pae, W. E., Rosenberg, G., Donachy, J. H., et al.: Mechanical circulatory assistance for postoperative cardiogenic shock: A three-year experience. *ASAIO Trans* 26:256–260, 1980; Pennington, D. G., Kanter, K. R., McBride, L. R., et al.: Seven years' experience with the Pierce-Donachy ventricular assist device. *J Thorac Cardiovasc Surg* 96:901–911, 1988). The Abiomed BVS-5000, also an extracorporeal device, is fixed vertically at the patient's bedside and is attached to the heart with percutaneous cannulae that exit the patient's chest below the costal margin (Champsaur, G., Ninet, J., Vigneron, M., et al.: Use of the Abiomed BVS System 5000 as a bridge to cardiac transplantation. *J Thorac Cardiovasc Surg* 100:122–128, 1990).

The most frequently used implantable systems for clinical application include the Novacor VAD (Novacor Division, Baxter Health Care Corp.) and the Heartmate (Thermocardiosystems) (Rowles, J. R., Mortimer, B. J., Olsen, D. B.: Ventricular Assist and Total Artificial Heart Devices for Clinical Use in 1993. *ASAIO J* 39:840–855, 1993). The Novacor uses a solenoid-driven spring to actuate a dual pusher plate. The pusher plate compresses a polyurethane-lined chamber which causes ejection of blood (Portner, P. M., Jassawalla, J. S., Chen, H., et al: A new dual pusher-plate left heart assist blood pump. *Artif Organs* (Suppl) 3:361–365, 1979). Likewise, the Heartmate consists of a polyurethane lined chamber surrounded by a pusher plate assembly, but a pneumatic system is used to actuate the pusher plate (Dasse, K. A., Chipman, S. D., Sherman, C. N., et al.: Clinical experience with textured blood contacting surfaces in ventricular assist devices. *ASAIO Trans* 33:418–425, 1987).

Efficacy of both the extracorporeal and implantable pulsatile systems has been shown (Rowles, J. R., Mortimer, B. J., Olsen, D. B.: Ventricular Assist and Total Artificial Heart Devices for Clinical Use in 1993. *ASAIO J* 39:840–855, 1993). However, certain complications are associated with the use of extracorporeal systems, including relatively lengthy surgical implantation procedures and limited patient mobility. The use of totally implantable systems raises concerns such as high cost of the device, complex device design, and again, relatively difficult insertion techniques.

Centrifugal pump VADs offer several advantages over their pulsatile counterparts. They are much less costly; they rely on less complicated operating principles; and, in general, they require less involved surgical implantation procedures since, in some applications, cardiopulmonary bypass (CPB) is not required. Thus, an implantable centrifugal pump may be a better alternative to currently available extracorporeal VADs for short- or medium-term assist (1–6 months). In addition, the use of centrifugal pumps in medium-term applications (1–6 months) may allow the more complex, expensive VADs, namely the Novacor and the Heartmate, to be used in longer term applications where higher cost, increased device complexity, and involved surgical procedures may be justified.

Prior art relating to centrifugal blood pumps is Canadian Patent No. 1078255 to Reich; U.S. Pat. No. 4,927,407 to Dorman; U.S. Pat. No. 3,608,088 to Dorman; U.S. Pat. No. 4,135,253 to Reich; Development of the Baylor-Nikkiso centrifugal pump with a purging system for circulatory support, Naifo, K., Miyazoe, Y., Aizawa, T., Mizuguchi, K., Tasai, K., Ohara, Y., Orime, Y., Glueck, J., Takatani, S., Noon, G. P., and Nose', Y., Artif. Organs, 1993; 17:614–618; A compact centrifugal pump for cardiopulmonary bypass, Sasaki, T., Jikuya, T., Aizawa, T., Shiono, M., Sakuma, I., Takatani, S., Glueck, J., Noon, G. P., Nose', Y., and Debakey, M. E., Artif. Organs 1992;16:592–598; Development of a Compact Centrifugal Pump with Purging System for Circulatory Support; Four Month Survival with an Implanted Centrifugal Ventricular Assist Device, A. H. Goldstein, MD; U.S. patent application titled "Radial Drive for Implantable Centrifugal Cardiac Assist Pump", University of Minnesota; Baylor Multipurpose Circulatory Support System for Short-to-Long Term Use, Shiono et al., ASAIO Journal 1992, M301.

Currently, centrifugal pumps are not implantable and are used clinically only for CPB. Examples include the Biomedicus and the Sarns centrifugal pumps. The Biomedicus pump consists of an impeller comprised of stacked parallel cones. A constrained vortex is created upon rotation of the impeller with an output blood flow proportional to pump rotational speed (Lynch, M. F., Paterson, D., Baxter, V.: Centrifugal blood pumping for open-heart surgery. *Minn Med* 61:536, 1978). The Sarns pump consists of a vaned impeller. Rotation of the impeller causes flow to be drawn through the inlet port of the pump and discharged via the pump outlet port (Joyce, L. D., Kiser, J. C., Eales, F., et al.: Experience with the Sarns centrifugal pump as a ventricular assist device. *ASAIO Trans* 36:M619–M623, 1990). Because of the interface between the spinning impeller shaft and the blood seal, several problems exist with both these pumps, including excessive wear at this interface, thrombus formation, and blood seepage into the motor causing eventual pump failure (Sharp, M. K.: An orbiting scroll blood pump without valves or rotating seals. *ASAIO J* 40:41–48, 1994; Ohara, Y., Makihiko, K., Orime, Y., et al.: An ultimate, compact, seal-less centrifugal ventricular assist device: baylor C-Gyro pump. *Artif Organs* 18:17–24, 1994).

The AB-180 is another type of centrifugal blood pump that is designed to assist blood circulation in patients who suffer heart failure. As illustrated in FIG. 1, the pump consists of seven primary components: a lower housing 1, a stator 2, a rotor 3, a journal 4, a seal 5, an impeller 6, and an upper housing 7. The components are manufactured by various vendors. The fabrication is performed at Allegheny-Singer Research Institute in Pittsburgh, Pa.

The rotor 3 is in the lower housing 1 and its post protrudes through a hole in the journal 4. The impeller 6 pumps blood in the upper housing 7 and is threaded into and rotates with the rotor 3. The impeller shaft passes through a rubber seal 5 disposed between the upper housing 7 and the journal 4, rotor and stator assembly. The upper housing 7 is threaded into the lower housing 1 and it compresses the outer edge of a rubber seal 5 to create a blood contacting chamber. In this manner, blood does not contact the rotor 3, journal 4, or lower housing 1. The upper housing 7 is connected to an inlet and outlet flow tubes 8, 9, called cannulae, that are connected to the patient's circulatory system, such as between the left atrium, LA, and the descending thoracic aorta, DTA, respectively. Through this connection, blood can be drawn from the left atrium, LA, through the pump, and out to the aorta, DTA.

The impeller 6 spins by means of the rotor 3 and stator 2 which make up a DC brushless motor. The base of the rotor 3 has four magnets that make up two north-south pole pairs which are positioned 90 degrees apart. The stator 2 is positioned around the rotor 3 on the lower housing 1. The stator 2 comprises three phases. When it is energized, it creates a magnetic force that counteracts the magnets in the rotor 3 causing the rotor 3 and impeller 6 to spin, as is well known with brushless DC motors.

A peristaltic pump infuses lubricating fluid into a port of the lower housing to lubricate the spinning rotor. The fluid prevents contact between any solid internal pump components during pump activation. It forms a layer of approximately 0.001 inches around the rotor and the impeller shaft. This fluid bearing essentially allows wear-free operation of the pump. The fluid passes around the rotor and flows up along the rotor post. Eventually, it passes out through the rubber seal 5 and into the upper housing 7 at the impeller shaft/seal interface. Fluid does not escape through the outer periphery of the housing seal because the upper housing is tightened down and sealed with a rubber O-ring to prevent leakage.

The spinning impeller 6 within the top housing 7 causes fluid to be drawn from the inlet flow tube 8 toward the eye of the impeller. The impeller 6 then thrusts the fluid out to the periphery of the upper housing 7. At this point, the fluid is pushed through the outlet tube 9 by centrifugal force. The pump typically consumes 3–5 Watts of input power to perform the hydraulic work necessary to attain significant physiologic benefits.

The prior art AB-180 pump has certain drawbacks which limit its efficacy as a cardiac assist device. The present invention describes several discoveries and novel constructions and methods which vastly improve such a pump's operation.

SUMMARY OF THE INVENTION

The present invention pertains to a blood pump device. The blood pump device comprises a blood pump having blood transport ports and cannulae connected to the ports. The blood pump device also comprises a coating material covering the junction between the inner surfaces of the ports and cannulae. This forms a smooth transition so blood can flow unimpeded therefrom and collection cavities for the blood are eliminated. The invention is also related to a method of producing a smooth coating.

The present invention is a blood pump device comprising a second portion having a stator mechanism and a rotor mechanism disposed adjacent to and driven by the stator mechanism. The second portion has a journal disposed about the rotor mechanism to provide support therewith. The second portion has an impeller disposed in the chamber and a one-piece seal member for sealing about a shaft of the impeller. The seal member is fixedly attached to the journal so that the seal member is supported by the journal.

Preferably, the rotor has a rotor post connected to the impeller shaft and an end adjacent to the seal member. The end has rounded edges to prevent abutment against any adhesive material disposed between the seal member and the journal.

The present invention is also a blood pump device which has an infusion port for providing lubricant material about the rotor, the infusion port has an inner diameter greater than 0.05 inches for minimizing pressure needed to introduce lubricant material into the blood pump.

The present invention is also related to means for providing power to the blood pump so that blood can be pumped through a cannulae. The providing means includes a controller having means for sensing pump failure and an output terminal for actuating a safety occluder in an event of pump failure. Preferably, there is a safety occluder device disposed about the cannulae and in communication with the output terminal. Preferably, the blood pump comprises a motor having stator mechanism and a rotor mechanism driven by the stator mechanism. The sensing means comprises means for determining back electromagnetic force within the stator mechanism. Preferably, the controlling means has means for providing signals indicate of stator current and rotor speed, respectively. The providing means is in communication with the means for determining back electromagnetic force in the stator mechanism.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
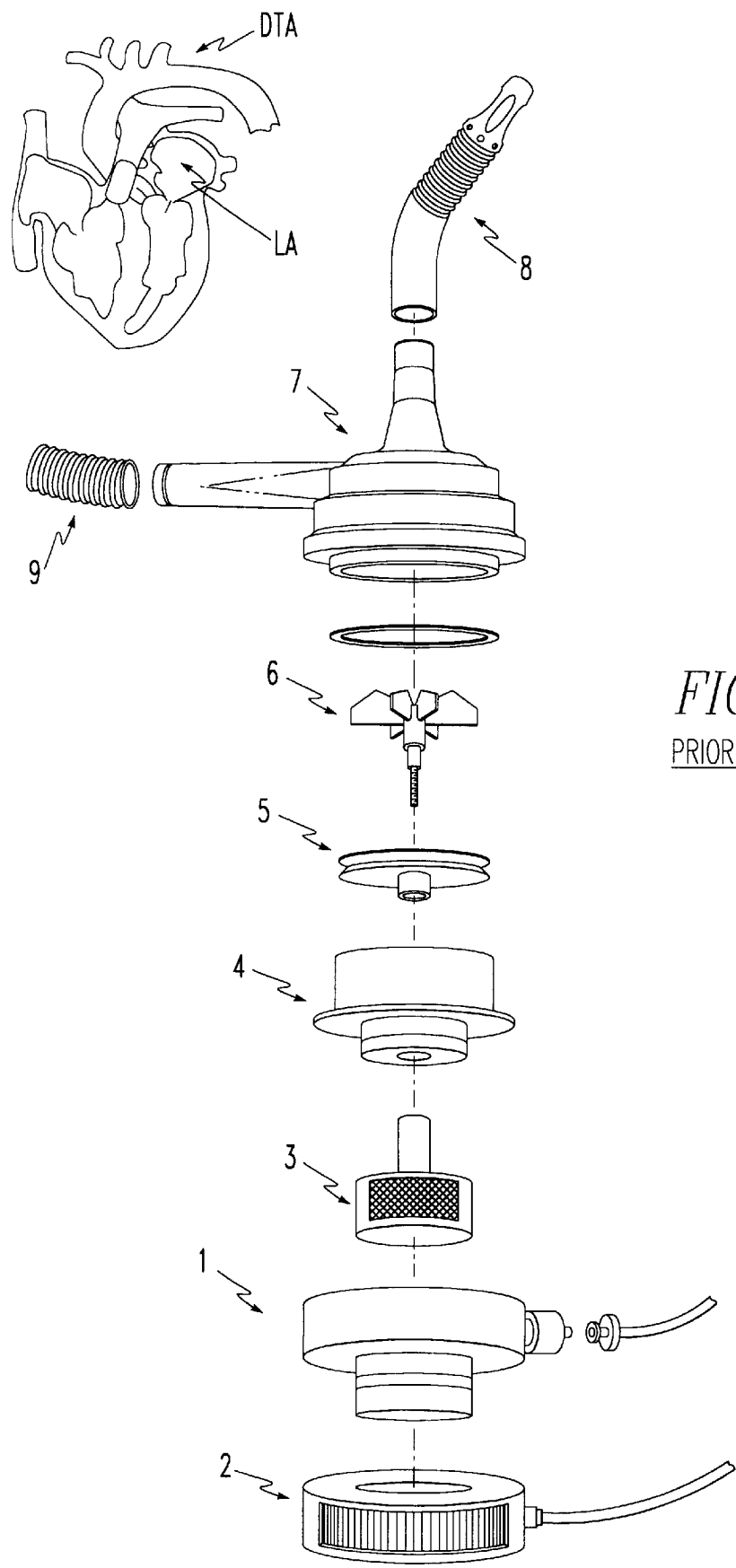
FIG. 1 is a schematic representation showing a centrifugal blood pump device of the prior art.
Figure 2:
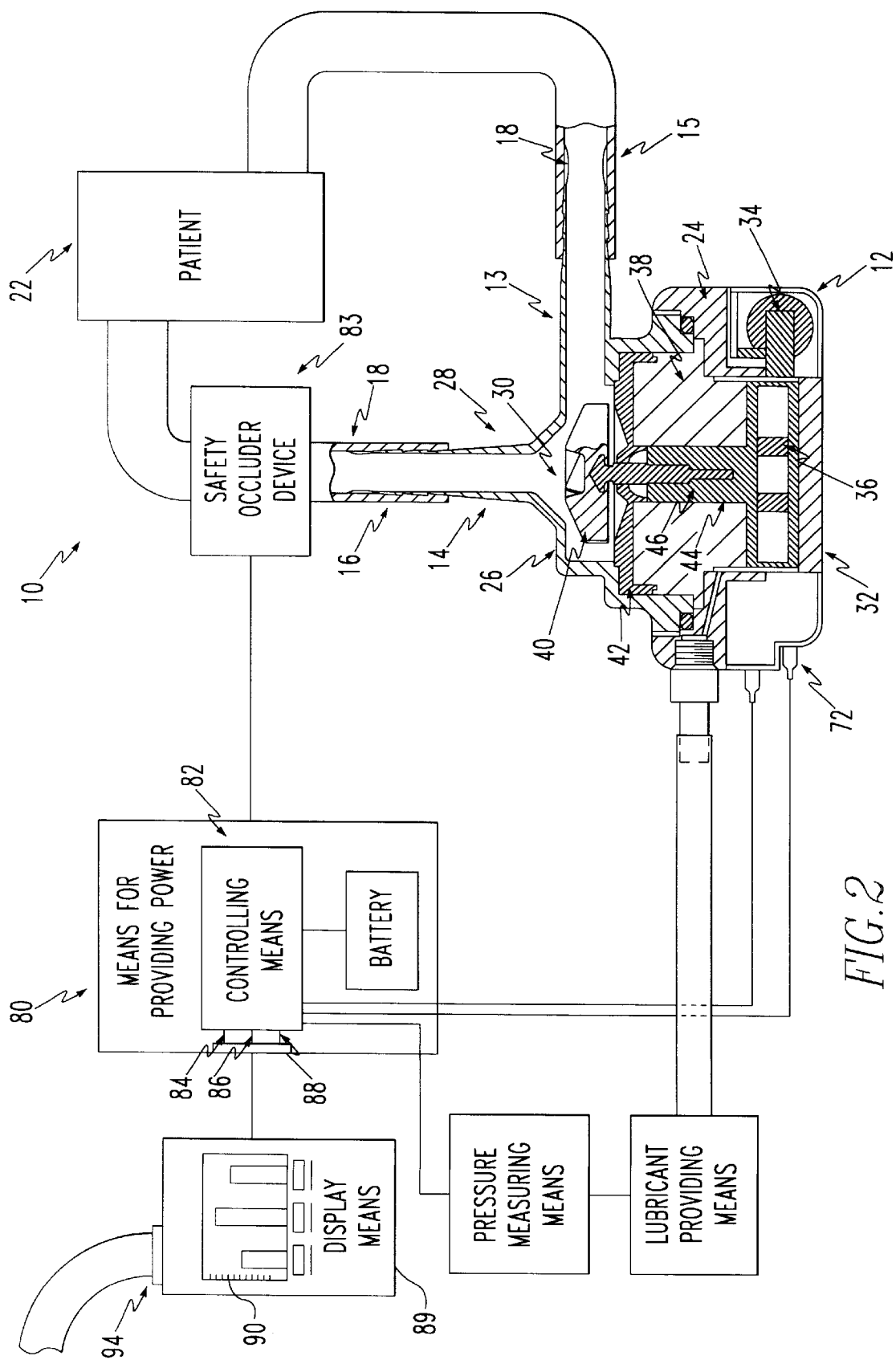
FIG. 2 is a schematic representation showing the blood pump device of the present invention and an associated system.

Referring now to the drawings wherein like reference numerals refer to similar or identical parts throughout the several views, and more specifically to FIG. 2 thereof, there is shown a blood pump device 10. The blood pump 10 comprises a blood pump 12 having a blood transport port 14 and a cannulae 16 connected to the port 14. As best shown in FIG. 3b, the blood pump device 10 also comprises a coating material 18 covering the junction between the inner surfaces of the port 14 and cannulae 16 so that a smooth transition surface 20 is formed and blood can flow smoothly therefrom and collection cavities for the blood are eliminated.

The inlet cannulae 16 can be inserted into the left atrium of the patient 22 and fixed with a double purse string suture. The outlet cannulae 15 can be sewn to the aorta of the patient 22. The inner junctions of the cannulae 15, 16 are coated with a polyurethane coating material 18 such as Biomer, manufactured by Ethicon, Inc. The coating material 18 provides a smooth transition surface 20 for the blood to flow on. This uniform transition is essential for reduction of clot formation.

The technique used to apply this coating material 18 is novel. It involves applying the polyurethane material 18 to the collection cavity 93 at the cannulae/port internal interface with a needle and syringe. After the polyurethane 18 is deposited, it is distributed evenly by hand rotation of the housing.

Figure 9:
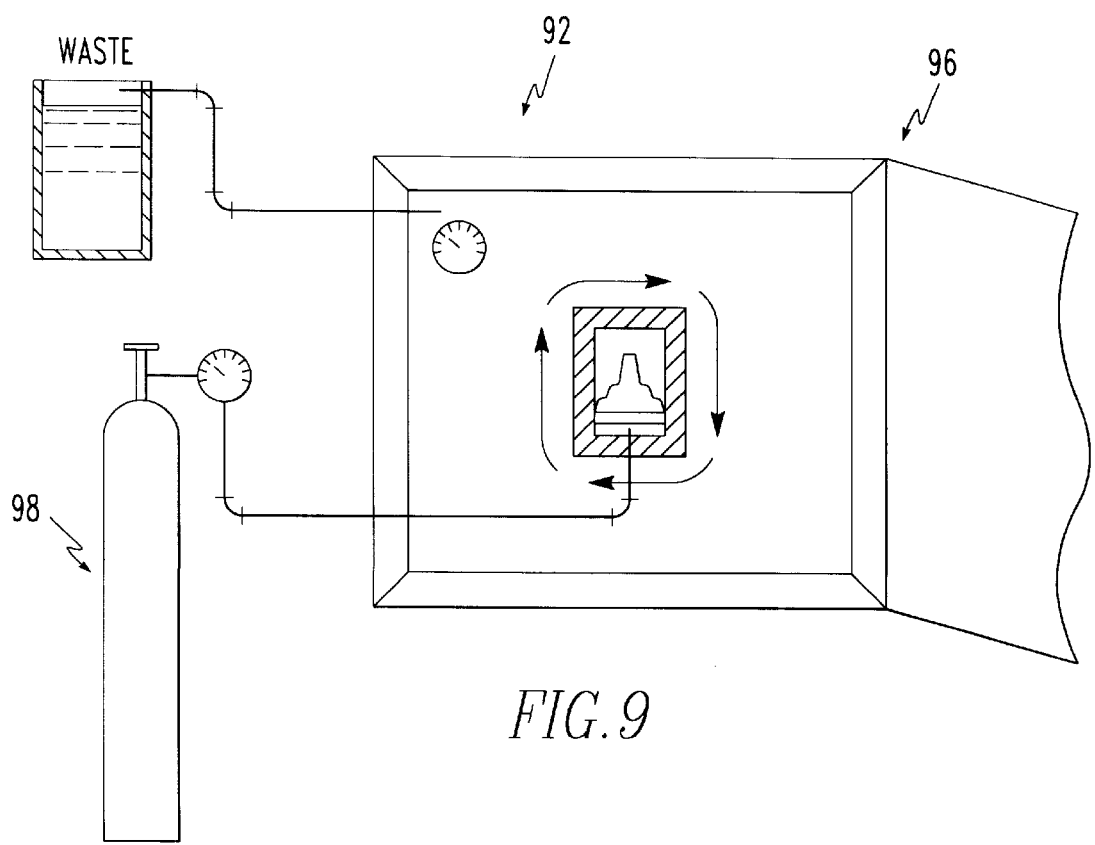
FIG. 9 is a schematic representation showing the cannulae coating apparatus.

Next, as shown in FIGS. 9 and 10, the upper housing 26 is spun axially for each cannula 15, 16 in a motor driven coating chamber 92 for 24 hours. This promotes more uniform distribution of the polyurethane 18 and allows full curing. It also assures that the polyurethane coating 18 fills the step-off between the housing ports and the cannulae. The coating chamber 92 consists of a motor shaft 94 enclosed by a plexiglass box 96. The shaft 94 is connected to a variable speed motor 95 protruding through the rear of the box. Nitrogen is passed through a jig 97 which fastens to the motor 95 and holds the pump housing 26 and cannulae 15, 16. The jig 97 directs nitrogen from container 98 to pass over the junction being coated. The nitrogen carries away the solvent gases from the polyurethane 18 that would otherwise attack and degrade other areas of the pump housing 26. The custom jig 97 functions to hold the top housing 26 in both configurations, one for coating the inlet flow cannulae 15 and the other for coating the outlet flow cannulae 17. Once the polyurethane 18 is cured and evenly distributed, the housing 26 is removed and the process is repeated for the other cannula.

Figure 3A:
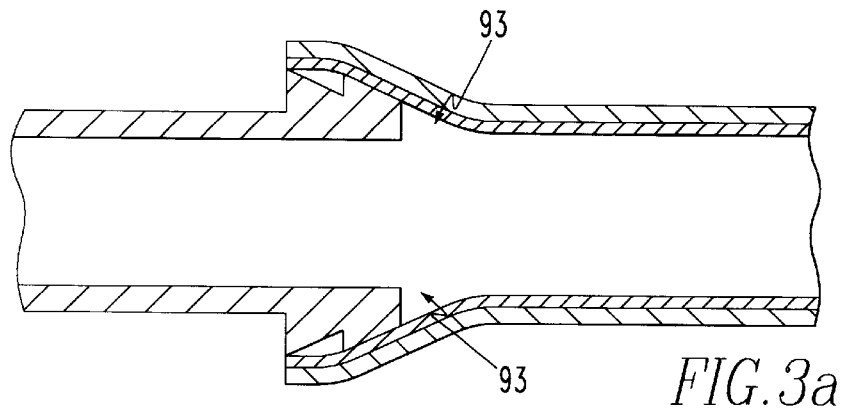
FIGS. 3a and 3b are schematic representations showing a blood collection cavity at the junction between port and cannulae and coating material over the junction between port and cannulae, respectively.
Figure 3B:
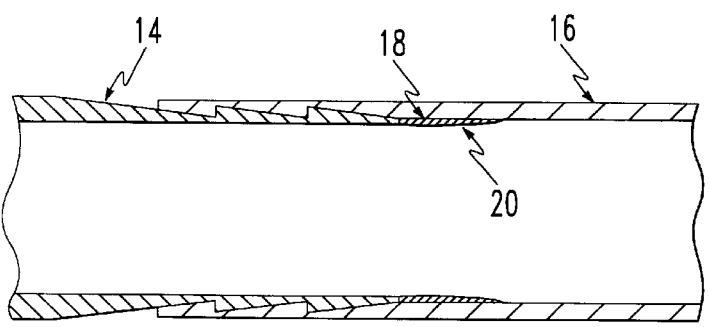

As shown in FIG. 3a, a prior art pump without the coating technique forms a collection cavity 93. The prior art blood pump was implanted in 14 sheep in an experiment from December 1988 to October 1990. (Modified Fabrication Techniques Lead to Improved Centrifugal Blood Pump Performance, John J. Pacella et al., presented at the 40th Anniversary Meeting of the American Society for Artificial Internal Organs, San Francisco, Calif., April 1994, incorporated by reference herein). The pump was arranged extra-corporeally in a left atrial to descending aortic cannulation scheme and the animals survived up to 13 days with the implanted prior art device. These experiments revealed that a major problem of the prior art pump was thrombus formation within the collection cavity 93 at the cannulae/housing interfaces.

In contrast, using the described antithrombogenic coating technique with coating material 18, 44 sheep were implanted with the blood pump device from 1992–1993 for periods of 1 day to 154 days and no thrombus was found at the interface. This represents a 100% success rate to date.

As shown in FIG. 2, the blood pump device 10 comprises a first portion 28 having a chamber 30 and an inlet and outlet port 13, 14 in fluidic communication with the chamber 30. The blood pump device 10 also comprises a second portion 32 having a stator mechanism 34 and a rotor mechanism 36 disposed adjacent to and driven by the stator mechanism 34. Together, the stator mechanism 34 and the rotor mechanism 36 form the motor 888. Preferably, the motor 888 is a brushless DC motor (BLDC) 888. The second portion 32 has a journal 38 disposed about the rotor mechanism 36 to provide support therewith. The second portion 32 also has an impeller 40 disposed in the chamber 30 and a one-piece seal member 42 for sealing about a shaft of the impeller 40. The seal member 42 is fixedly attached to the journal 38, such as with adhesive, so that the seal member 42 is supported by the journal 38. Preferably, the seal member 42 comprises a coating surrounding and sealing its outer surface. Further, the rotor 36 preferably has a surface 44 which has been polished to a surface finish of less than 2.54 μm for enhanced low friction operation. The amount of material removed from the rotor 36 during the polishing process is less than 0.0001 inches (2.54 um).

Figure 4A:
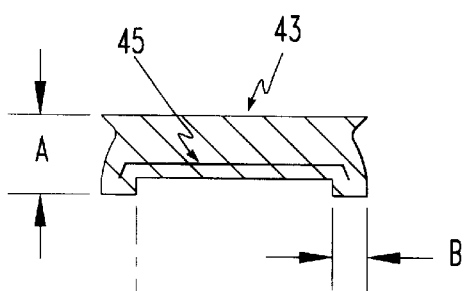
FIGS. 4a and 4b are schematic representations showing a prior art seal construction and the present inventions seal construction, respectively.
Figure 4B:
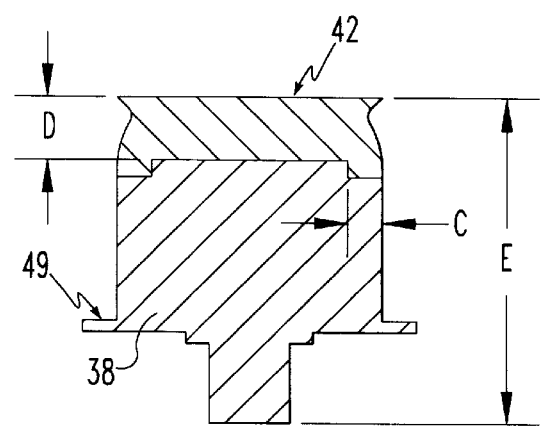

As shown in FIGS. 4a and 4b, the hard plastic journal 38 and seal member 42 is fastened together, such as with Loctite 401 adhesive, to achieve seal stiffness, which was previously provided by the metal insert 45 molded into the prior seal 43. Also, the seal member 42 can be coated with Biomer (Ethicon, Inc.) polyurethane for enhanced antithrombogenicity.

Two improvements in pump characteristics have been made through this new seal 42. First, the cost of production of the seal member 42 has been decreased significantly. The prior seal 43 had a metal insert 45 that was required to maintain seal stiffness, since the seal 43 is made of soft, flexible rubber. The disclosed construction of the present invention eliminates the need for an insert and simplifies the molding process. The seal member 42 is glued directly to the journal 38, which is made of hard plastic, to achieve overall seal stiffness. The process of gluing these two components is simple and relies on an inexpensive adhesive. Second, this insert 45 had to be machined separately placed in the rubber seal 43. As a result, the fabrication process of the seal left metallic sections of the insert 45 exposed to fluid contamination and therefore prone to rust. Since the seal member 42 of the present invention eliminates the insert, no steel is present for potential iron oxidation.

Further, the overall height, E, of the journal/seal assembly has been increased from approximately 0.928 inches to 0.944 inches. This has resulted in a tighter seal at the junction between the outer rim 49 of the seal member 42 and the top housing 26, decreasing the chance for blood stasis and clot formation. As the top housing 26 is tightened down upon the lower housing 24 through their threaded connection, it compresses the outer rim 49 of the seal 42. The increased journal/seal height allows this compression to occur closer to the beginning of the threads. In other words, the upper housing does not need to be rotated as far through the threads to achieve the same tightness as it would if the journal/seal height, E, was not increased. Because of this, there is more room to achieve a tighter seal.

The following are preferred dimensions of the seal constructions shown in FIGS. 4a and 4b:

A=0.273 in.
B=0.208 in.
C=0.06 in.
D=0.192 in.
E=0.944 in.

The journal/seal design, as shown in FIG. 4b, has been used in the disclosed sheep implantation studies and has functioned superbly. Results of the studies have shown inconsequential quantities of thrombus around the periphery of the top housing 26 in a few cases and none in the majority of the studies.

Figure 5A:
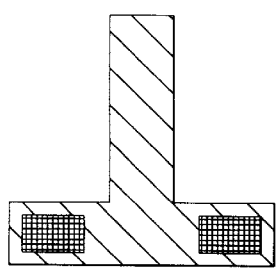
FIGS. 5a and 5b are schematic representations showing a prior art rotor post and the rotor post of the present invention, respectively.
Figure 5B:
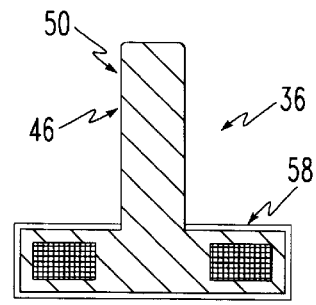

As best shown in FIG. 5b, the top edge 50 of the rotor post 46 is preferably rounded to allow a better fit under the seal member 42. The rotor post 46 is inserted into the journal 38 and fits just beneath the seal member 42. The junction between the journal 38 and the seal member 46 occurs at this point and the two components are affixed with adhesive (i.e. Loctite 401). The rounding of the edge 50 on the rotor post 46 prevents the rotor 36 from rubbing against any excess glue that may be present after the seal member 42 and journal 38 are fastened together.

The surfaces of the rotor 36 are preferably polished to 2.54 μm and given a rust-proof coating 58. Results from the sheep studies have revealed little evidence of rust and polished surfaces have been shown to greatly increase durability between the rotor 36 and journal 38 and between the rotor 56 and the lower housing 60.

Figure 6A:
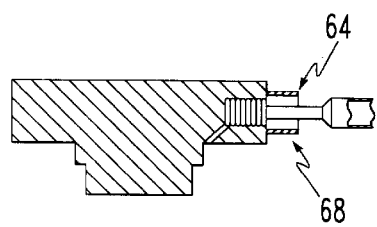
FIGS. 6a and 6b are schematic representations showing a prior art infusion port and the infusion port of the present invention, respectively.
Figure 6B:
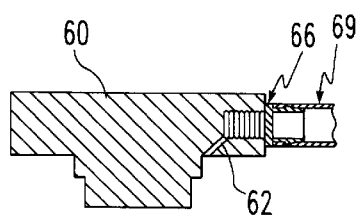

As best shown in FIGS. 6a and 6b, the infusion port 62 is preferably enlarged from 0.03 inches to 0.062 inches. The housing 24 and port 62 can also be cryogenically deburred. Further, a ¼ 28 UNF male luer lock 66 is used instead of the prior ¼ 28 UNF threaded hex barb 68 to eliminate the male-female junction 64 at this point.

The port 62 serves as a passageway for pump lubricant, such as water or saline, which is delivered to the pump and exits through the rubber seal member 42 into the blood stream. The port 62 is enlarged because it assists in attaining lower pump lubricant pressures, which diminishes the stress on all lubricant system components. Also, a small port is more likely to become occluded with debris (e.g. salt deposit from lubricant saline solution) and cause increases in lubricant pressures.

The male-female junction 64 in the previous design (FIG. 6a) was eliminated to decrease the chance of foreign debris in the chest cavity from infiltrating into the lubricant system. The use of a threaded barb 66 helps to solve this problem because there is one less junction. The threaded end is screwed into the lower housing 60 and chemically sealed and the barbed end is inserted directly into the lubricant tubing 69 creating a mechanical seal.

The deburring of the housing 60 results in increased durability and improved pump performance and lower internal lubricant temperatures. The internal lubricant temperature was measured by inserting an Omega, Inc. 33 Gauge hypodermic needle thermocouple directly through the pump baffle seal, just below the lip of the seal where the lubricant passes out. We found that rough (undeburred) component surfaces of the prior pump resulted in internal lubricant temperatures of 50° C. The lubricant temperatures of a pump device 10 with polished, deburred components was found to be 42–43° C., which is significantly less. Since heat is thought to be a possible contributor to thrombus formation, this ay have increased the antithrombogenicity of the pump as well as increasing its durability.

Figure 7A:
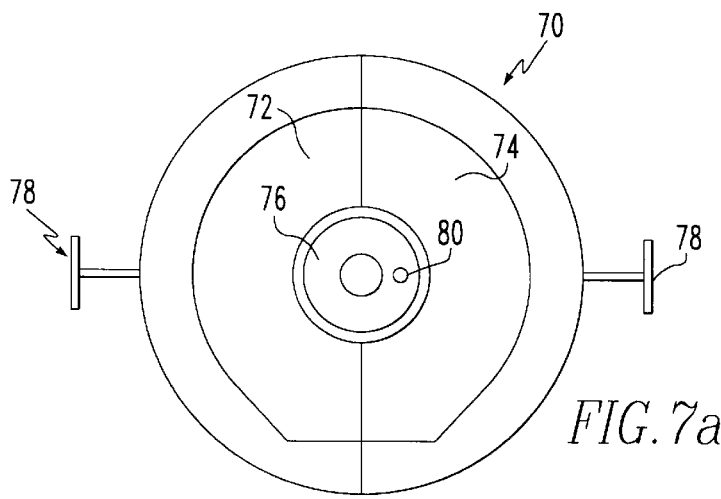
FIGS. 7a and 7b are schematic representations showing a mold for casting the stator of thermally conductive epoxy.
Figure 7B:
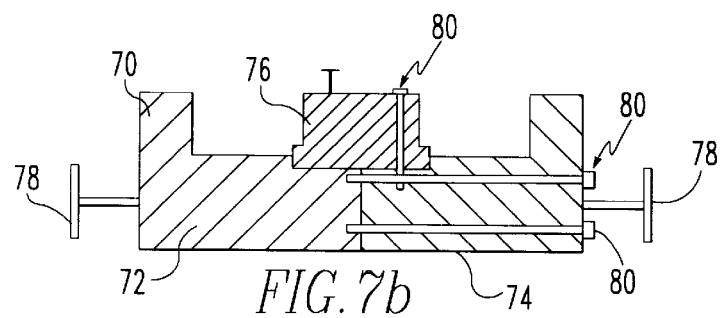
Figure 8:
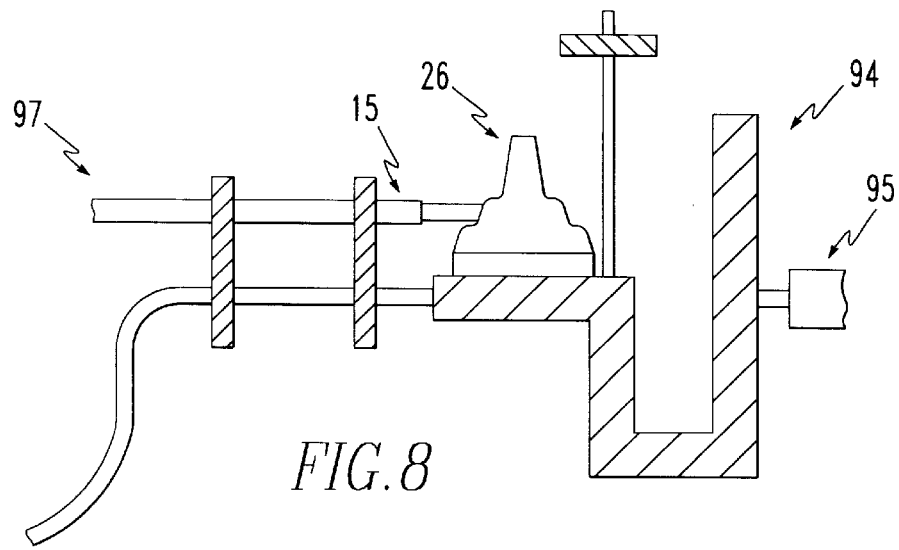
FIG. 8 is a schematic representation showing the housing jig of the cannulae coating apparatus.

As shown in FIGS. 7a and 7b, a new mold 70 was designed for stator fabrication. New, thermally conductive epoxy material is used for fabricating the stator 34. The new mold 70 has two halves 72, 74, a removable center stem 76 and handles 78 for quick releasing of the halves 72, 74. Fastening bolts 80 hold the halves 72, 74 and center stem 76 together. The mold 70 has significantly increased the quality of the stator 34 as indicated by the progressive increases in the survival times of sheep in the disclosed blood pump implantation studies. In chronological order, the five studies of durations greater than ten days were 14, 10, 28, 35, and 154 day durations. The new mold 70 was used in the 35 and 154 day studies.

Thermally conductive epoxy material was used for stator fabrication to help carry heat away from the stator 34 and allow it to conduct readily to the surrounding tissues. As a result, the present stator 34 with thermally conductive epoxy has surface temperatures rarely exceeding 2.5° C. above ambient temperature versus 5–7 C. in the 14 and 10 day studies. Referring to FIG. 2, environmentally sealed connectors 72 replace older style connectors used for controller/stator electrical connections. Further, the stator 34 can be dip coated in polyurethane before potting.

Figure 12A:
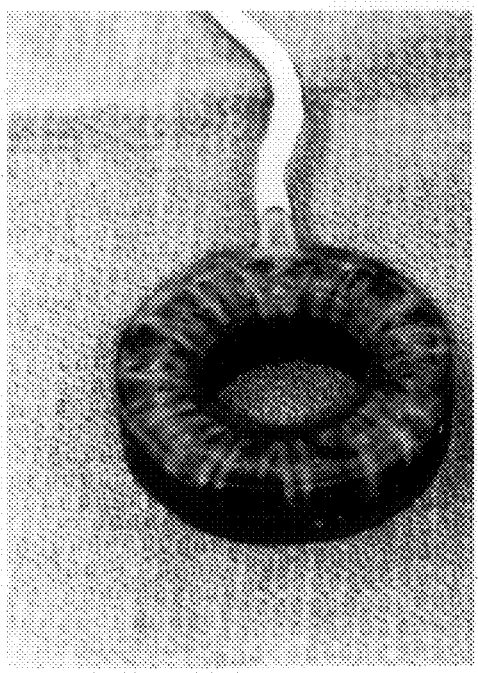
FIGS. 12a and 12b are photographs showing the prior art stator and the stator of the present invention, respectively.
Figure 12B:
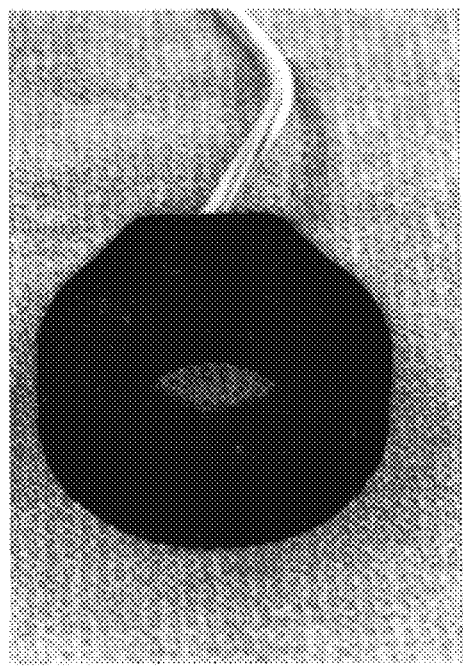

A commercially available environmentally sealed connector 72 (LEMO USA, Inc.) is preferably used to prevent the electrical connections from failing in the event of exposure to fluid. The prior art connector was not waterproof. To hermetically seal the stator 34, it can be dipped in polyurethane several times during the fabrication process. FIGS. 12a and 12b show the prior art stator and the stator 34 of the present pump device 10.

The control means 80 of the present invention preferably has an output 82 for actuation of a safety occluder device 83 in the event of motor failure. Also, there are standardized outputs for current 84, speed 86, and lubricant system pressure 88 (0–1 Volt). The controller 80 uses isolated circuitry to cut down on noise by stator commutation. Three meters 90 of a display means 81, with both digital and bar graph output show the outputs.

The automated occluder initiation output 82 greatly enhances safety for in vivo use of the blood pump. In the event of motor failure, detected by back the EMF sensor means 92, the controller 80 will activate the safety occluder device 83 to prevent retrograde pump flow through the cannulae 16. If pump current becomes zero, the controller 80 will attempt to restart the pump five times and if it is unsuccessful, it will send a signal to actuate the occluder device 83 through output 82. The increased reliability allows more time for intervention and troubleshooting. The standardized analog outputs for current 84, speed 86, and perfusion pressure 88 (0–1 volt) provides enhanced and comprehensive data collection. The outputs 84, 86, 88 can be used for trend recording on a strip chart recorder 94, as opposed to direct measurements once a day. Furthermore, isolated circuitry and display means 89 with three meters 90 with both digital and bar graph output with ±1% accuracy on all readings prevent noise caused by stator commutation and provides reliable data collection.

Figure 13:
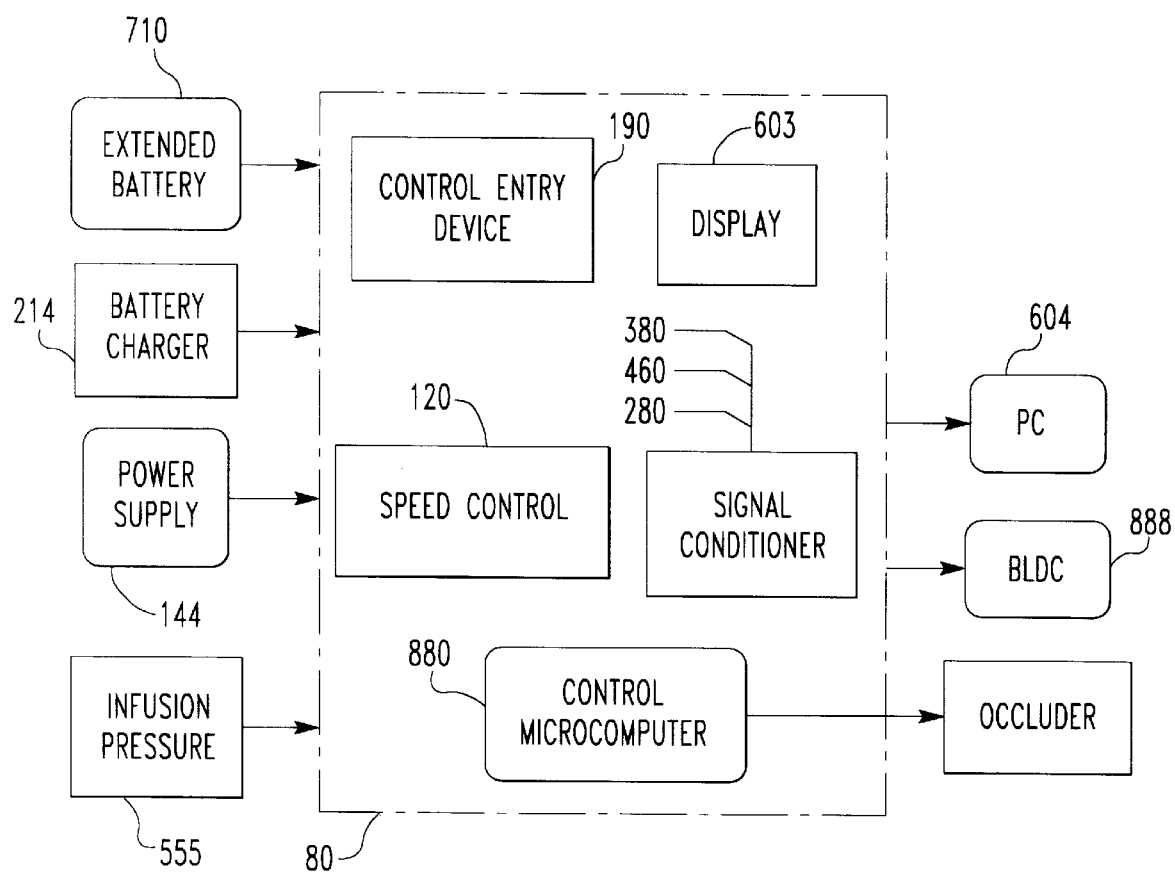
FIG. 13 is a block diagram of one embodiment of the sensorless blood pump controller in accordance with the present invention showing the external connections to the personal computer BLDC motor (blood pump device), occluder, extended battery supply, power supply, and infusion pressure input.

The controller in more detail is shown in FIG. 13.

Figure 14:
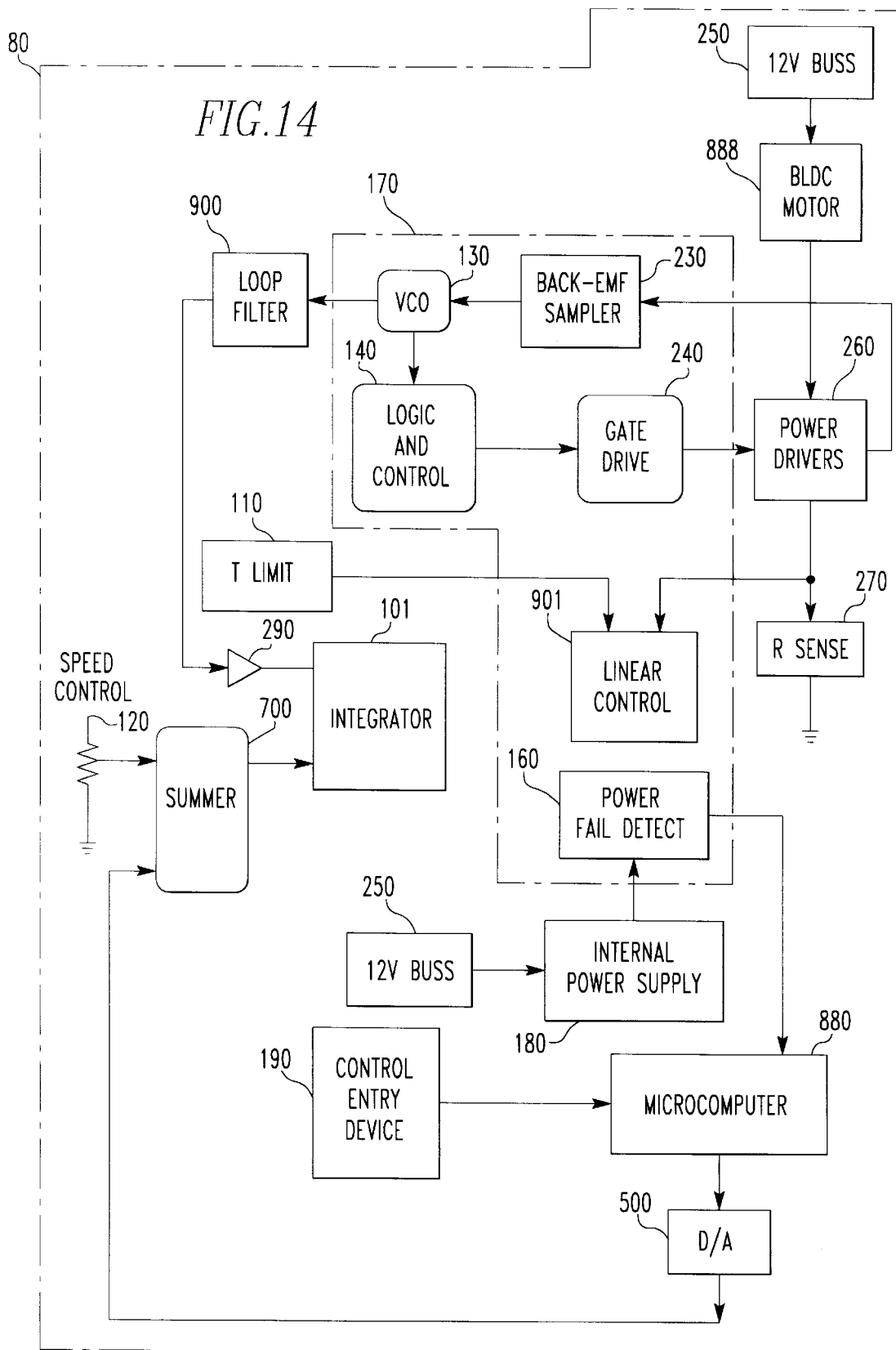
FIG. 14 is a block diagram of one embodiment of the sensorless blood pump controller in accordance with the present invention showing the components that control and regulate and monitor the operation of the sensorless blood pump controller.

The sensorless blood pump controller 80 is preferably used to control the motor 888. It is called sensorless because no sensors are disposed in the pump 12 itself. Referring to FIG. 14, a block diagram is provided of the preferred embodiment of many possible embodiments of the sensorless blood pump controller 80.

A highly integrated control I.C. 170, such as ML4411 available from Microlinear, San Jose, Calif., is comprised of the VCO 130 connected to a Back-Emf sampler 230 and to a logic and control 140. The control I.C. 170 also includes gate drivers 240 for connection to power driver 260, linear control 901 connected to power driver 260 and I limit 110 and integrator 101 and R sense 270. The control I.C. 170 additionally includes power fail detect 160. The ML4411 I.C. 170 provides commutation for the BLDC motor 888 utilizing a sensorless technology to determine the proper phase angle for the phase locked loop. The function and operation of the specific features and elements of the control I.C. 170 itself is well known in the art. Motor commutation is detected by the Back-EMF sampler 230.

For closed loop control, loop filter 900, connected to VCO 130 and amplifier 290, charges on late commutation, discharges on early commutation and is buffered by a non-inverting amplifier 290, model LM324 available from National Semiconductor, Santa Clara, Calif. The buffered output provides feedback to the integrator 101 that includes an inverting amplifier, model LM324. Preferably, non-inverting amplifier 290 and integrator 101 with an inverting amplifier are disposed on one chip. The speed control 120 uses a 20K ohm dailpot, model 3600S-001-203 available from BOURNS, Riverside, Calif. The speed control 120 in conjunction with summer 700 provides the set point for integrator 101. The output from the integrator 101 is used in conjunction with the input from R Sense 270, 0.05 ohms, part number MP821-.05, available from Caddock Electronics, Riverside, Calif., to the linear control 901 to modulate gate drivers 240. The power drivers 260 consists of six N– channel field effect transistors, part number RFP70N03, available from Harris Semiconductor, Melbourne, Fla. The power drivers 260, connected to the gate drivers 240, drive the BLDC motor 888.

The integrator 101 receives the desired speed control from the speed control 120 and also receives a feedback signal from the control I.C. 170 through its Back-EMF sampler 23 which passes the speed of the rotor 36 in the BLDC motor 888. The output signal from the integrator 101, which essentially is an error correction signal corresponding to the difference between the speed control set point signal and the sensed velocity of the rotor mechanism 36 of the BLDC motor 888, is provided to the linear control 901. The linear control 901, with the error correction voltage signal from the integrator 101 and the voltage signal from the R sense 270, which corresponds to the stator mechanism 34 current, modulates the gate drivers 240 to ultimately control the current to the stator mechanism 34 of the DC motor 888. The R sense 270 is in series with the power drivers 260 to detect the current flowing through the power drivers 260 to the stator mechanism 34 windings of the BLDC motor 888.

Power fail detect 160, an open collector output from the ML4411 control I.C. 170, is active when the +12 VDC or the +5 VDC from the power supply 180 is under-voltage. The power fail detect 160, alerts the microcomputer 880 that a fault condition exists.

Figure 15:
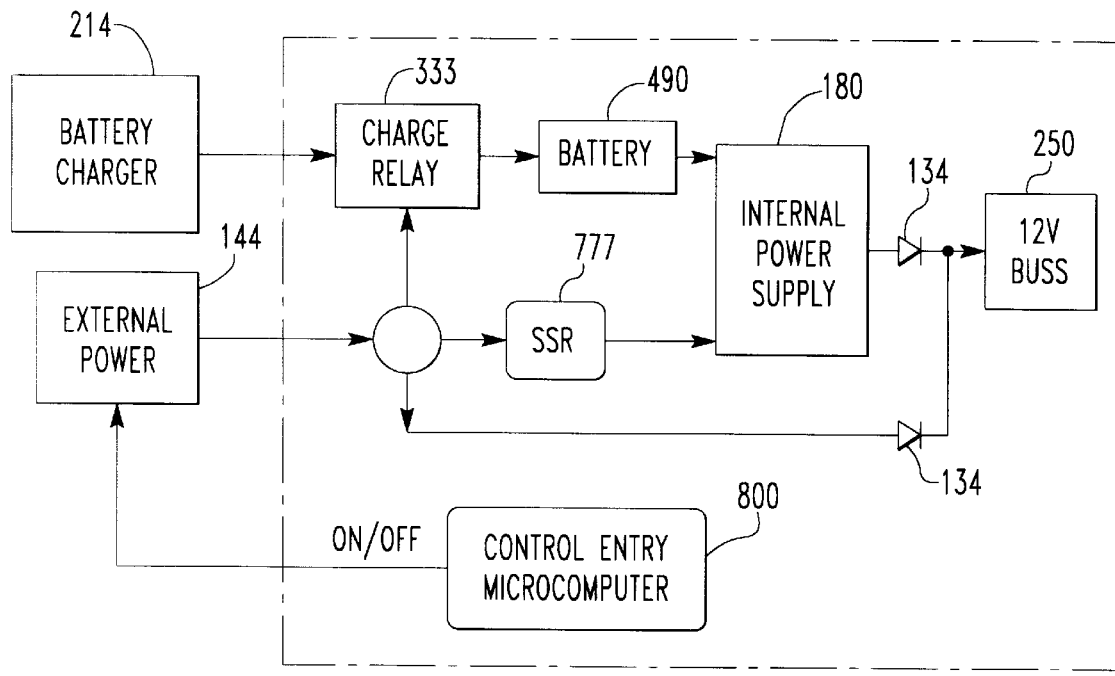
FIG. 15 is a block diagram of one embodiment of the sensorless blood pump controller in accordance with the present invention showing the internal power supply, external power supply, battery back-up, and battery charger circuits.

Referring to FIG. 15, external power supply 144 provides 12 VDC for the sensorless controller 80. Switching the external power supply 144 on or off is accomplished by the on/off control entry microcomputer 800. A logic '1' gates the external power supply 1 off and vice-versa. Battery back-Up is accomplished by solid state relay 777, P.N. AQV210, available from AROMAT, New Providence, N.J. When external power is lost, the internal power supply 180, P.N V1-J01-CY, available from Vicor, Andover, Mass. is enabled. The internal power supply 180 which derives power from the battery 490 P.N. V1-J01-CY, available from Vicor, Andover, Mass. is enabled. The internal power supply 180 derives power from the battery 490 P.N. 642-78002-003, available from GATES, Gainsville, Fla. Charge relay 333, P.N. 81H5D312-12, available from Potter and Brumfield, Princeton, Ind. switches out the external battery charger 214 when the control entry microcomputer 800 is 'ON'. Schottky diode 134, P.N. MBR1545, available from International Rectifier, Segundo, Calif., performs a logic 'OR' on the External Power 144 or Internal power supply 180 to the 12 V Buss 250.

Figure 16:
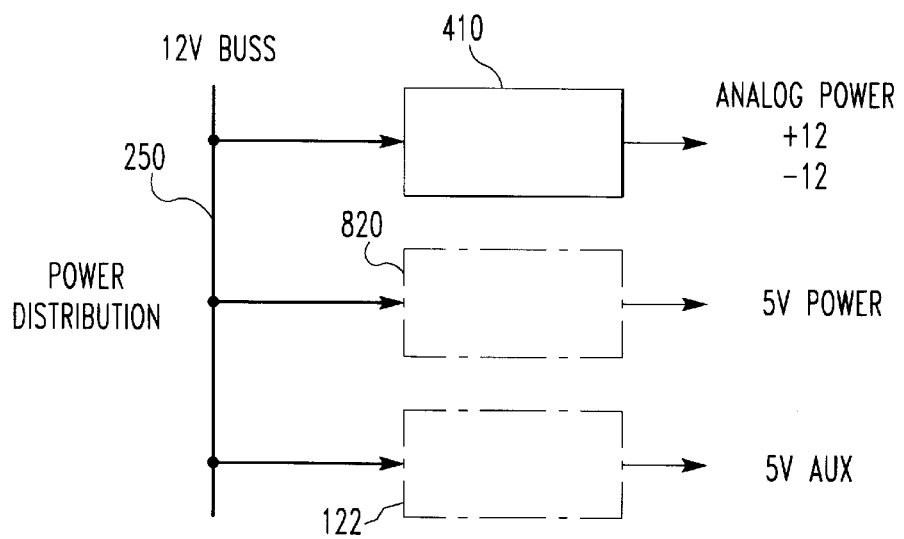
FIG. 16 is a block diagram of one embodiment of the sensorless blood pump controller in accordance with the present invention showing the power distribution.

Referring to FIG. 16, power is derived from the 12 V Buss 250 and feeds DC to DC converter 410, P.N. NME1212S, available from International Power Sources, Ashland, Mass. and provides +12,–12 V for the Analog circuitry. The DC/DC converter 820, P.N. 78SR105 available from Power Trends, Batavia, Ill. provides +5 VDC power for the DVM's and the control I.C. 170. The DC/DC converter 122, P.N. 11450, available from Toko America, Prospect, Ill. provides +5 VDC to the microcomputer 880.

Figure 17:
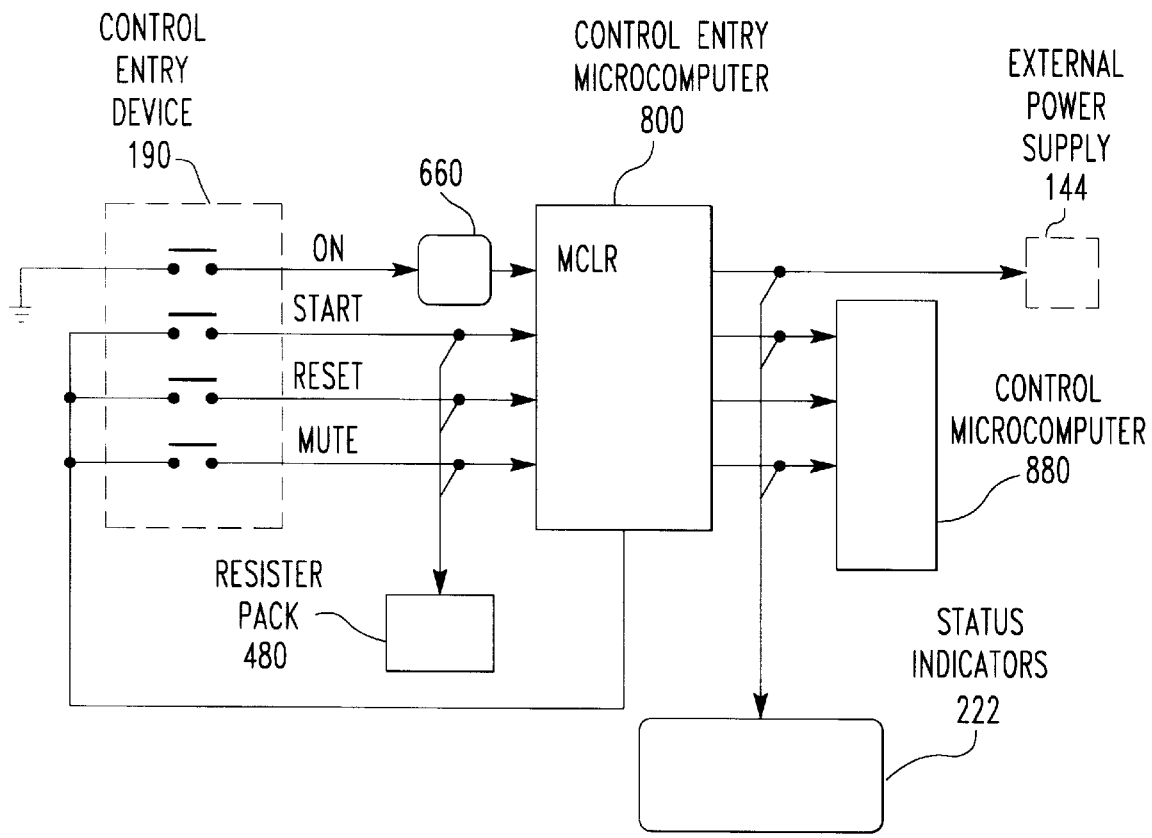
FIG. 17 is a block diagram of one embodiment of the sensorless blood pump controller in accordance with the present invention showing the Control Entry Device as used with the control entry microcomputer and the control computer.
Figure 18:
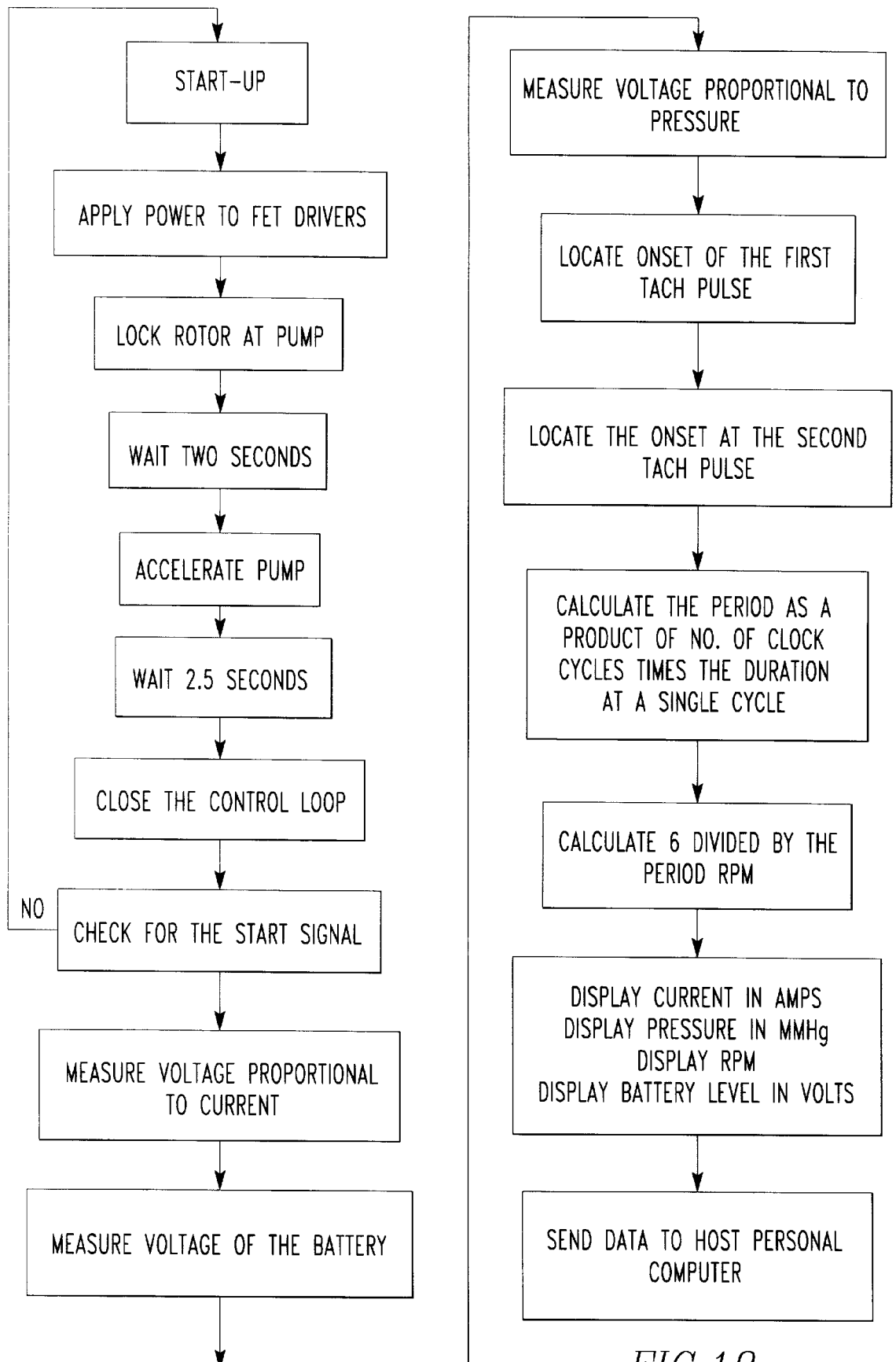
FIG. 18 is a flowchart showing the start-up sequence for the motor, the measurement of the pump parameters, display of pump parameters, and downloading of pump parameters to an IBM personal computer.
Figure 19:
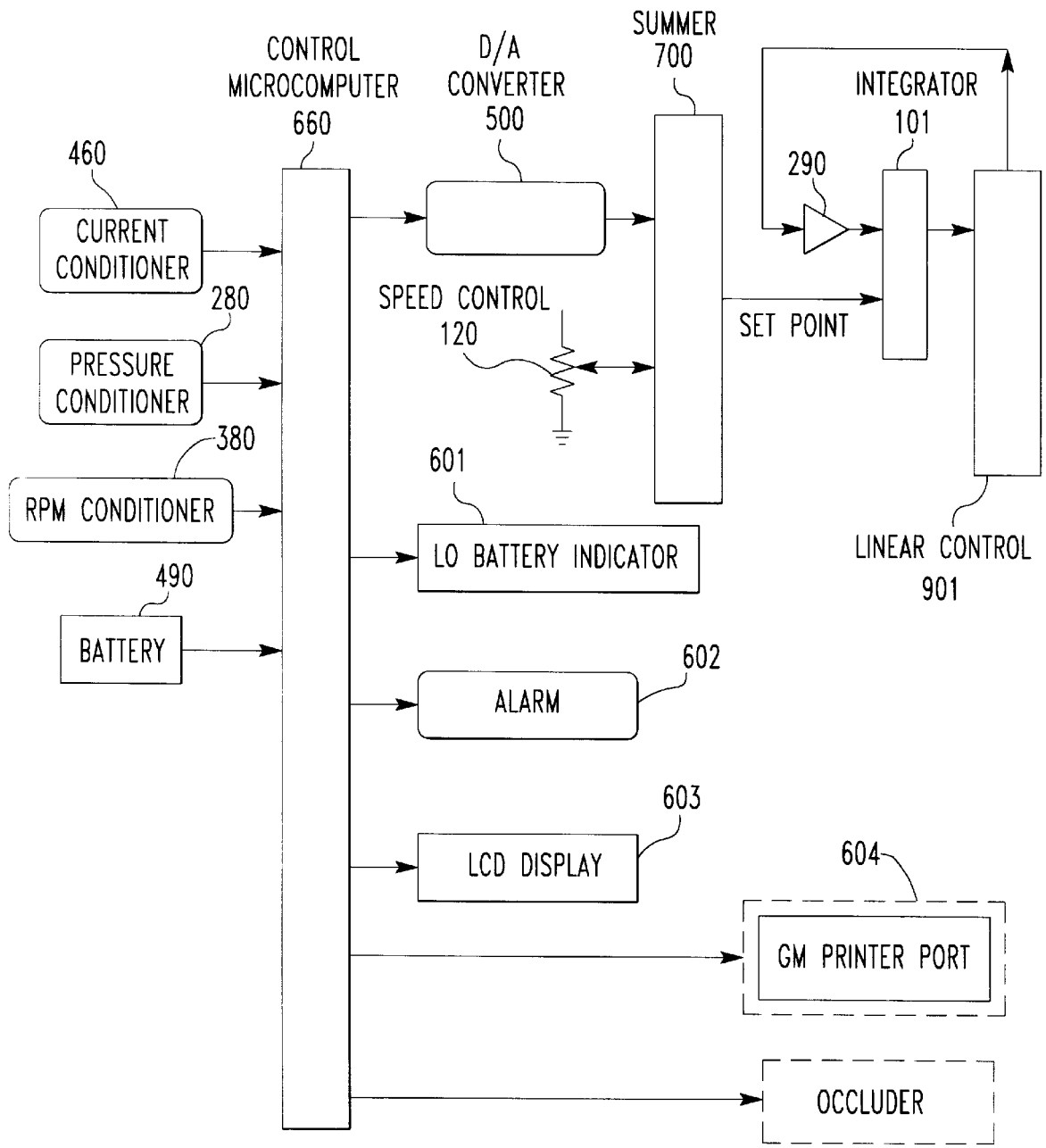
FIG. 19 is a block diagram of one embodiment of the sensorless blood pump controller in accordance with the present invention showing the signal conditioner inputs to the control microcomputer, the output that compensates for a retrograde flow, the alarm that is activated for low infusion pressure, the low battery indicator, the occluder output, the alphanumeric LCD display, and the connection to an external IBM computer.

Referring to FIG. 17, depression of the "ON" switch, p/o of switch assembly of the control entry device 190, P.N. 15.502, available from Solico/MEC, Hartford, Conn., discharges capacitor (RC) p/o external reset circuit 660 initiating a reset signal to the Control Entry microcomputer 800, P.N. PIC16C54, available from Microchip, San Jose, Calif. The control entry computer 800 toggles an I/O line to signal the External Power Supply 144 to power up and to turn status indicator 222 on. The START, RESET, and MUTE lines from 190 are connected to resistor pack 480 P.N. R-9103-10K, available from Panasonic, Secacus, N.J. The control entry microcomputer 800, sends control lines including START, RESET, and MUTE to the control microcomputer 880, P.N. PIC16C71, available from Microchip, San Jose, Calif. and to the Status Indicators 222, P.N. 16.921-08, available from Solic/MEC, Hartford, Conn. Depressing the START on control entry device 190 causes the Control Entry microcomputer 800, to assert the START signal to Control microcomputer 880. The Control microcomputer 880 initiates the sequence to start the motor 888. Refer to FIG. 18. Upon successful completion of the START routine, referring to FIG. 19, the control microcomputer 880, digitizes three analog inputs including current conditioner 460 connected to the motor 888, Infusion Pressure conditioner 280 and the internal battery voltage 490. The Control I.C. 170 is connected to the RPM conditioner 380. The control microcomputer 880 is connected to the RPM conditioner 380. Referring to FIG. 18, the control microcomputer 880 measures the period of the RPM input and calculates the RPM. Referring to FIG. 19, the control microcomputer 880 updates the LCD Display 603, P.N. 97-20947-0, available from EPSON, Terrance, Calif. and downloads the data including RPM, current, infusion pressure, and battery voltage to the external connection connecting the SBPC to the IBM printer port 604. The control microcomputer 880 is connected to the alarm 602, P.N. P9923, available from Panasonic, Secaucus, N.J. and is activated when the infusion pressure is low. See FIG. 20. Upon an error detected with the retrograde flow, the control microprocessor 880 of FIG. 19, outputs ramped voltage to the digital to analog converter 500, P.N. MAX531, available from Maxim, Sunnyvale, Calif. The D/A converter 500 is connected to an analog summer 700. The speed control 120 is connected to the analog summer 700, which is part of four amplifiers in a package. P.N. LM324, available from national semiconductor, Santa Clara, Calif. The summer 700 is connected to the integrator 101. The integrator 101 is connected to the control I.C. 170.

Figure 20:
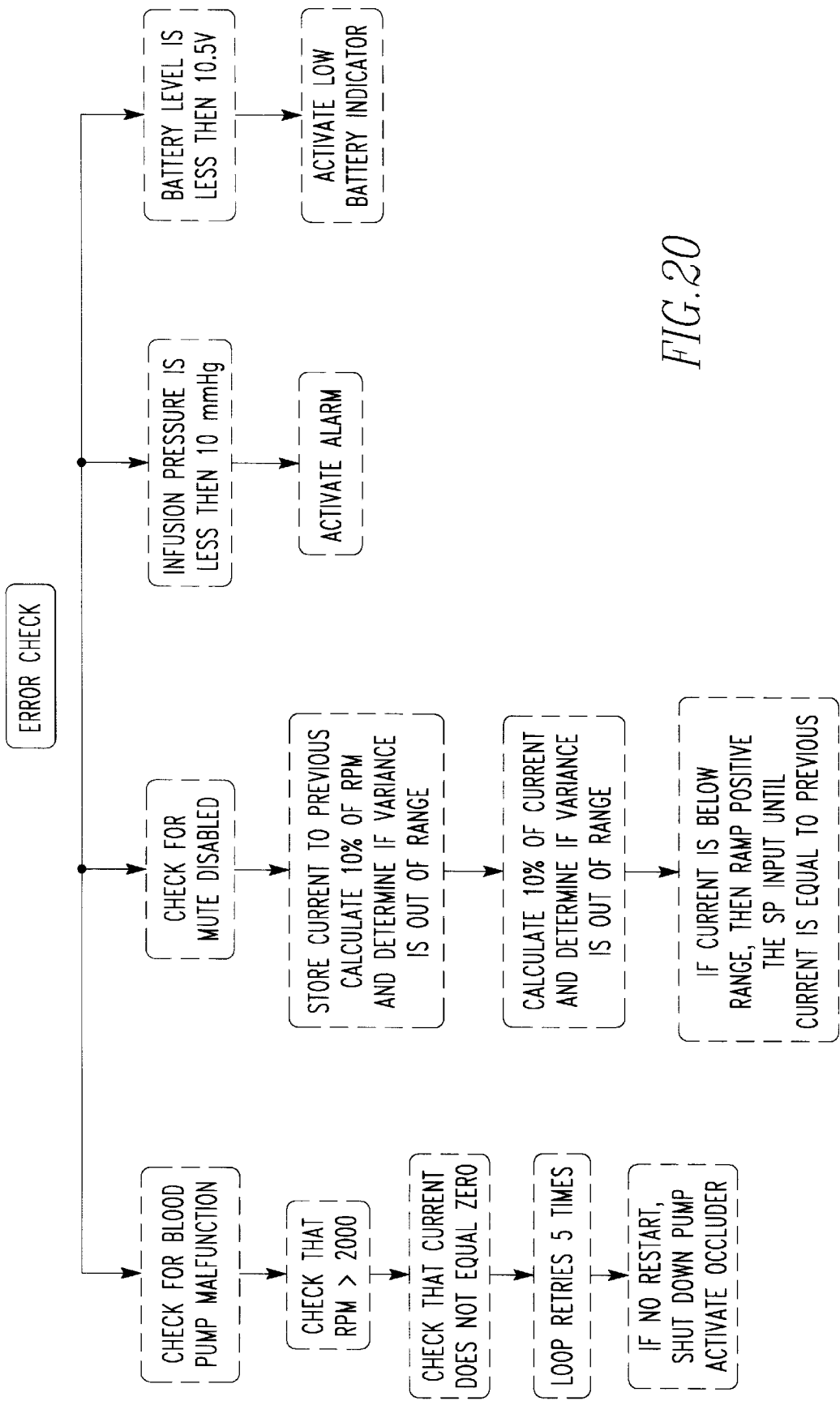
FIG. 20 is a flowchart of the error checks including blood pump malfunction, retrograde flow and low infusion pressure that results in a corrective action or alarm.

Referring to FIG. 20, the control microcontroller 880, upon detecting an error that RPM is less than 2000 or zero motor current tries to restart the motor 888 five times. After five times, if the motor 888 does not start, then the SBPC activates an external occluder. See U.S. patent application Ser. No. 08/228,150, filed Apr. 15, 1994, titled "Occluder Device and Method of Making", by John J. Pacella and Richard E. Clark, having attorney docket number AHS-3, incorporated by reference herein, filed contemporaneously with this application for a description of the occluder.

An implantable centrifugal blood pump for short and medium-term (1–6 months), left ventricular assist is disclosed in "Modified Fabrication Techniques Lead to Improved Centrifugal Blood Pump Performance", John J. Pacella et al., presented at the 40th Anniversary Meeting of the American Society for Artificial Internal Organs, San Francisco, Calif., April 1994. Pump operation such as durability and resistance to clot formation was studied. The antithrombogenic character of the pump 10 is superior to prior art pumps due to the coating 18 at the cannula-housing interfaces and at the baffle seal. Also, the impeller blade material has been changed from polysulfone to pyrolytic carbon. The electronic components of the pump have been sealed for implantable use through specialized processes of dipping, potting, and ultraviolet-assisted sealing. The surfaces of the internal pump components have been treated in order to minimize friction. These treatments include polishing, ion deposition, and cryogenic deburring. The pump device 10 has demonstrated efficacy in five chronic sheep implantation studies of 10, 14, 28, 35 and 113+ day durations. Post-mortem findings of the 14-day experiment revealed stable fibrin entangled around the impeller shaft and blades. Following pump modification with refined coating techniques and advanced impeller materials, autopsy findings of the ten-day study showed no evidence of clot. Additionally, the results of the 28-day experiment showed only a small (2.0 mm) ring of fibrin at the shaft-seal interface. In this study, however, the pump failed on day 28 due to erosion of the stator epoxy.

In the experiments of 35 and 113+ day durations, the stators were re-designed, and the results of both experiments have shown no evidence of motor failure. Furthermore, the 35-day study revealed a small deposit of fibrin 0.5 mm wide at the lip of the seal. Based on these studies, it can be ascertained that these new pump constructions have significantly contributed to the improvements in durability and resistance to clot formation. In this study, the pump device 10 was implanted in five sheep for a minimum of 10 days. Prior to surgery, the sheep were fasted for 24 hours, but were allowed unlimited access to water. The pump device 10 was implanted through a left thoracotomy and arranged in a left atrial-to-descending aortic cannulation scheme. Two percutaneous tubes were required for pump operation: one was used to jacket the conductors that supply power to the stator 34 and the other provided a conduit for pump lubricant infusion. The animals were infused at a constant rate with either 0.9% saline or sterile water as the pump lubricant. Daily measurements of pump speed, current, voltage, flow, animal body temperature, and stator surface temperature were obtained. The animals were free to ambulate within a 4-foot by 6-foot pen and were tethered to a custom-made swivel tether device as disclosed in U.S. Pat. No. 5,305,712. Weekly blood draws consisted of blood counts, electrolytes, coagulation profiles, hepatic and renal function, and hemolysis. Blood cultures were obtained as needed. The autopsy included complete histopathologic studies and a microscopic analysis of the pump 10.

Various modifications in the pump configuration throughout the course of the five studies were made to improve the antithrombogenicity, corrosion resistance, and durability of the pump. Antithrombogenicity was addressed by applying polyurethane coatings to the cannulae housing interface and the seal and substituting pyrolytic carbon for polysulfone as the impeller blade material. In addition, alterations in the lubricant infusion rate and the anticoagulation scheme were incorporated. The rotor surfaces 46 were conditioned through polishing and passivating procedures with the goal of increasing pump durability, and the lower housing rotor bearing surface was cryogenically deburred for the same purpose. Finally, the pump stator 34 was dip-coated in polyurethane and potted in a larger sized mold to provide more material coverage of the stator to increase the resistance of the pump to fluid corrosion.

Pump modifications were made continuously throughout the five studies, depending on the results of each preceding study, as shown below in Table I:

TABLE I

Result Dependent Modifications

| Modification | Experiment Duration (Days) | | | | |
|---|---|---|---|---|---|
| | 14 | 10 | 28 | 35 | 154 |
| Lower Housing Conditioning | | | | X | X |
| Rotor Conditioning | | | | X | X |
| Re-designed Stator | | | | X | X |
| Seal Coating | X | X | X | X | |
| Cannula/Housing Coating | X | X | X | X | X |
| Impeller Material | P | C | C[1] | C[1] | C[1] |
| Perfusion Flow Rate (ml/hr) | 2 | 4 | 10 | 10 | 10 |
| Anticoagulation | N | H,S | A,H,C,S | A,H,C,S | A,H,C,S,U |

Figure 10A:
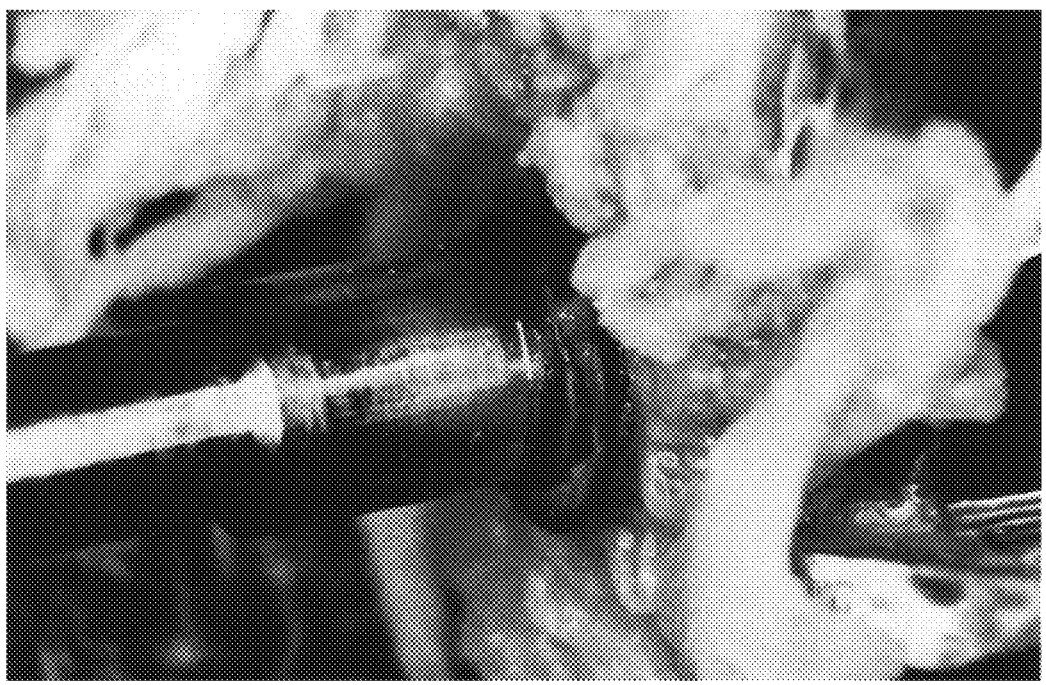
FIG. 10a is a photograph showing a massive clot on the impeller and at shaft/seal interface from the 14-day study.
Figure 11A:
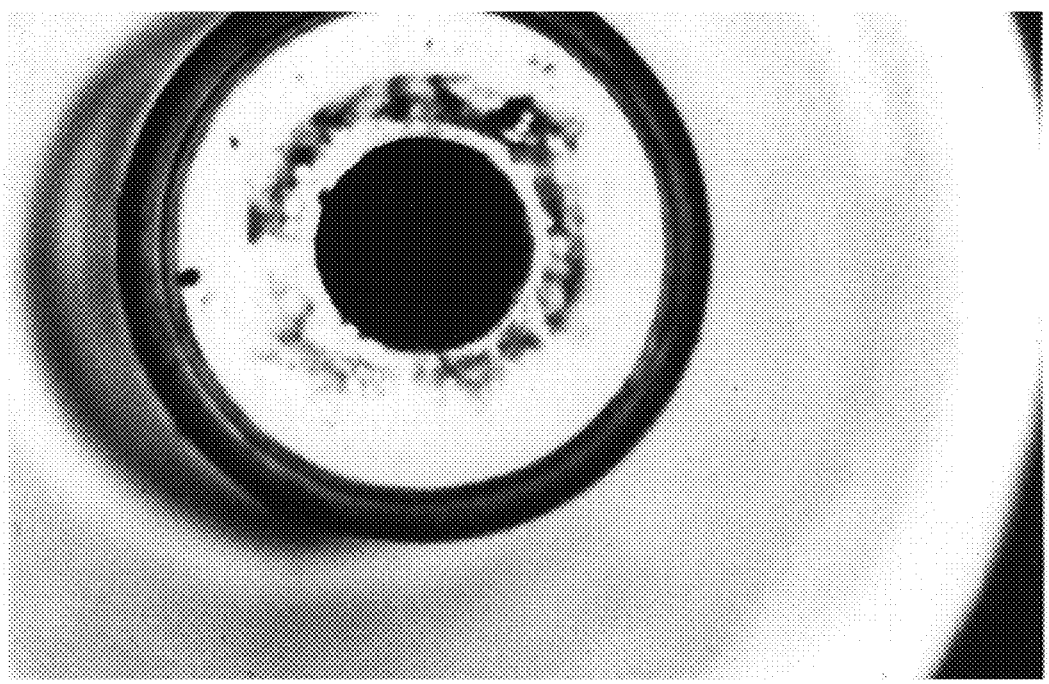
FIGS. 11a and 11b are photographs showing rust on the rotor in the 14-day study and no rust present in the 154-day study, respectively.

N = none; A = aspirin; H = heparin; C = coumadin; S = streptokinase; U = urokinase; P = polysulfone; C[1] = pyroltic carbon The 14-day study incorporated a prior art rotor and lower housing, a polysulfone impeller, and a polyurethane coating applied to the cannulae/housing interfaces. The lubricant flow rate was 2 ml/hr and no anticoagulants were used. Autopsy findings revealed a massive clot entangled within the impeller blades and fixed to the impeller shaft at the shaft/seal junction, as shown in FIG. 10a. The cannulae/housing interfaces were free to clot due to the sealing material 18. Rust was present on the rotor, as shown in FIG. 11a.

Figure 10B:
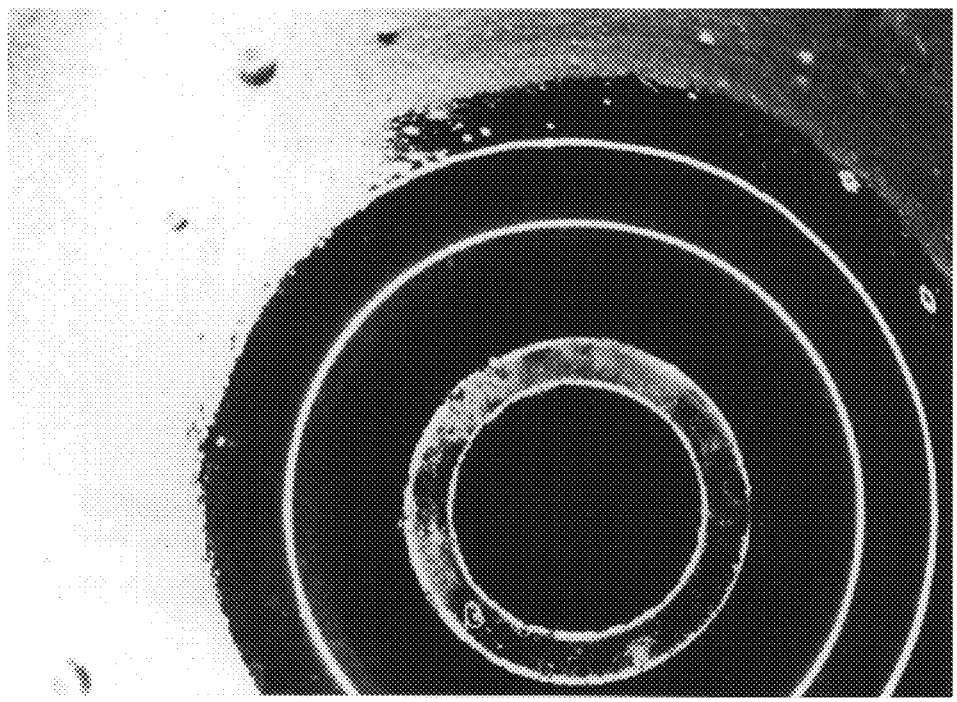
FIG. 10b is a photograph showing a clot-free pump seal in the 10-day study.

The second study of 10 days duration included pump alterations consisting of a polyurethane coating (Biomer, Ethicon, Inc.) applied to the seal 42, a pyrolytic carbon impeller 40, a 0.9% saline lubricant flow rate of 4 ml/hr, and the use of heparin in the saline lubricant. Streptokinase was administered every third day with the lubricant. The explanted pump was found completely devoid of thrombus, as shown in FIG. 10b.

Figure 10C:
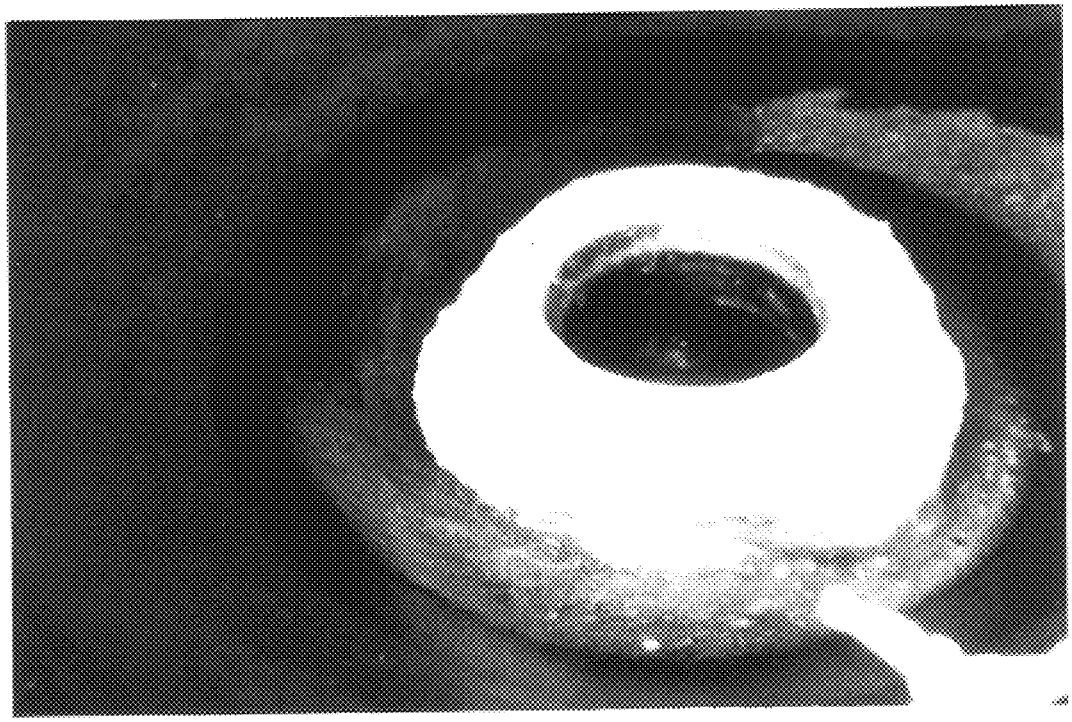
FIG. 10c is a photograph showing a 2 mm clot at the shaft/seal interface in the 28-day study.

In a third study of 28 days duration, the pump was arranged similarly to the 10-day study. However, the lubricant flow rate was increased to 10 ml/hr and 325 mg aspirin and 5–20 mg coumadin were given daily by mouth to broaden the anticoagulant regimen. A 2 mm ring thrombus was found at the impeller shaft/seal interface, as shown in FIG. 10c, and the motor was found to be contaminated by chest cavity fluid as indicated by chemical corrosion of select stator windings.

The fourth study of 35 days used several of the new pump components. These comprised a stator 34 with several polyurethane coatings and an increased epoxy potting thickness to prevent fluid corrosion, as shown in FIG. 12b. Also, a thin layer of titanium ion-coating was used to passivate the rotor surfaces 46 and reduce the opportunity for rust formation. Furthermore, the lower housing bearing surface was deburred to decrease wear on the rotor 36. The perfusion flow rate and anticoagulation scheme remained unaltered in this study. The explanted pump had a small irregular ring clot of 0.5 mm at its widest point surrounding the impeller shaft/seal junction. The pump lubricant system became completely occluded due to precipitation of salt from the saline solution. As a result, significant seepage of blood products below the seal caused increased friction between the rotor 36 and its bearing surfaces and eventually caused pump stoppage. However, there were no emboli at autopsy.

Figure 10D:
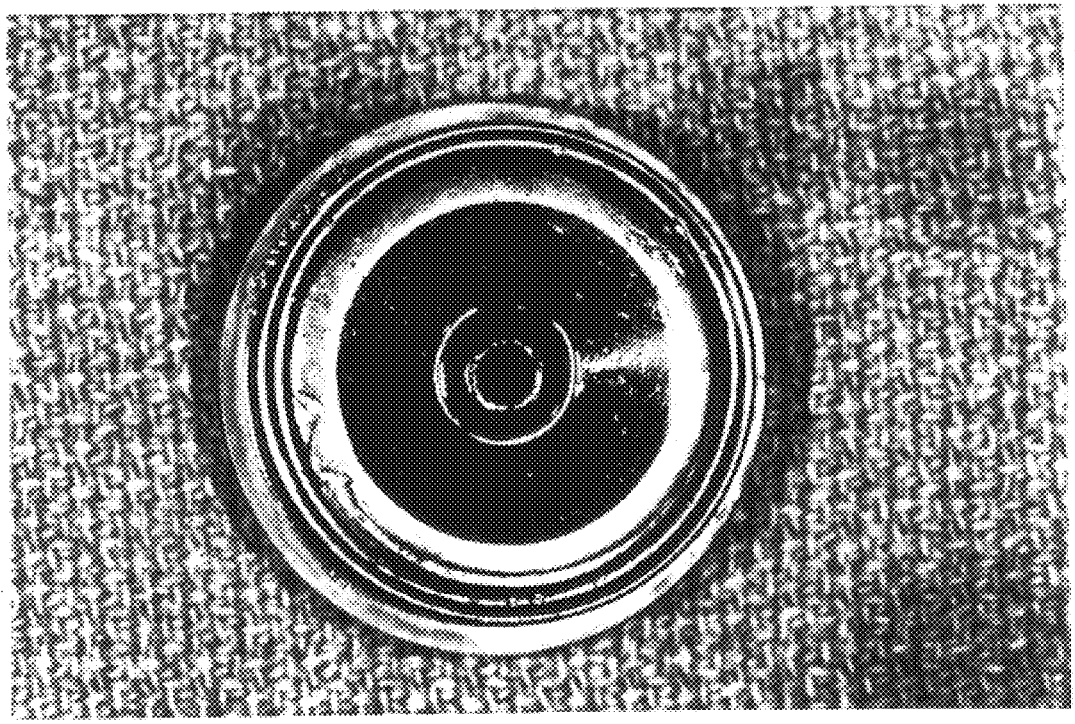
FIG. 10d is a photograph showing a clot-free pump seal in the 154-day study.
Figure 11B:
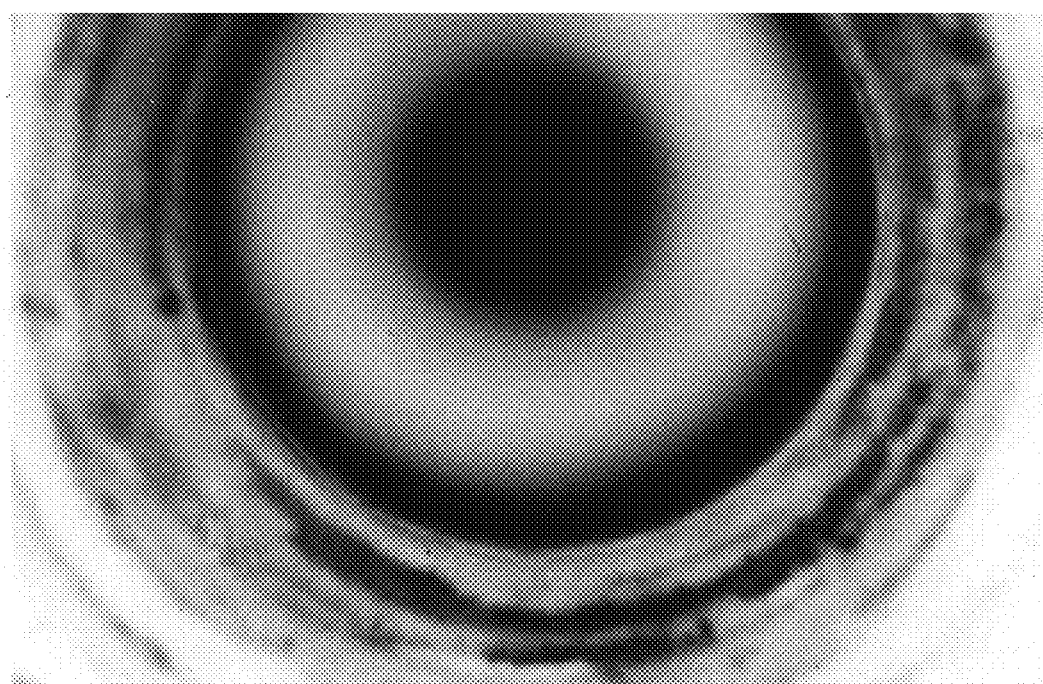

The last study of 154 days duration included variations from the previous study. For instance, thin layer chromium ion-coating was used in place of titanium coating to passivate the rotor 36 because it was available and cheaper. The lubricant was changed from 0.9% saline to sterile water on post-operative day (POD) 86 in order to reduce the chance of lubricant system occlusion due to salt precipitation. Next, based on published reports and preliminary studies of various antithrombotic drugs in sheep, urokinase was used as an alternative to streptokinase beginning on POD 130 because of its suspected superior thrombolytic effect. This study revealed a pump devoid of thrombus and free of measurable wear based on light microscopic and dimensional analysis, as shown in FIG. 10d. Furthermore, no evidence of rust was found on the rotor surface, as shown in FIG. 11b. However, the pump stator 34 completely failed due to fluid corrosion.

The lubricant rate was increased from 2 to 10 ml/hr over the course of the five studies. The intention was to increase fluid washing of the seal/impeller shaft interface to prevent blood stasis and thrombus formation. Precipitated salt was identified as a potential source of lubricant blockage in the 35-day study. As a result, the 154-day study underwent a change in lubricant from 0.9% saline to sterile water. The hematocrit and serum free hemoglobin measures were unaffected by this change.

Efficiency was calculated for each study by applying interpolation techniques to bench data of hydraulic performance and using pump input power as the product of pump voltage and current. Table II, shown below, shows stator temperature, animal body temperature, and their difference for each experiment. The average difference between the stator surface temperature and the animal core temperature decreased from 5.5–7° C. in the 14 and 10 day studies to approximately 1–3° C. in the 28, 35, and 154-day studies:

TABLE II

Average Values of Pump Efficiency, Stator Temperature, Animal Temperature, and Temperature Difference for Each Study

| Study Duration (days) | 14 | 10 | 28 | 35 | 154 |
|---|---|---|---|---|---|
| Pump Efficiency (%) | 13.6 ± 2.1 | 16.3 ± 4.7 | 20.5 ± 2.6 | 15.0 ± 1.6 | 13.2 ± 2.2 |
| Stator Temperature (° C.) | 45.4 ± 1.4 | 44.8 ± 1.4 | 41.8 ± 0.7 | 41.5 ± 0.7 | 41.6 ± 1.0 |
| Animal Temperature (° C.) | 39.2 ± 0.3 | 39.0[1] | 40.6 ± 0.7 | 39.0 ± 0.7 | 39.1 ± 0.6 |
| Temperature Difference[2] (° C.) | 6.8 ± 1.5 | 5.8 ± 1.4 | 1.3 ± 0.7 | 2.4 ± 0.5 | 2.6 ± 0.6 |

Note: All values are averages over the course of each study
[1]Measurement taken on first post-operative day only.
[2]Temperature Difference = Stator Temperature − Animal Temperature The novel construction of the pump device 10 contributed to overall improved pump performance as compared to previous pump devices. Conditioning of both the rotor 36 and lower housing surfaces has included polishing and passivating and cryogenic deburring, respectively. These techniques provide even distribution of lubricant over the moving components, smoother surfaces for direct contact in the event of lubricant system failure, and resistance to the oxidation of iron. These studies show that passivation of the rotor surfaces caused elimination of rotor rust, as evidenced by a comparison of the prior art rotor used in the 14-day study (FIG. 11a) with the chromium-coated rotor used in the 154-day study (FIG. 11b). The decreases in temperature difference between the stator and ambient can be related to increases in lubricant flow rate from 2 to 10 ml/hr (Table II).

Based on these five studies, the implications are that the temperature difference between the stator surface and ambient decreased by means of increased convective heat loss through higher lubricant infusion rates.

Also, since this pump relies on a fluid bearing between the rotor and its adjacent surfaces, no correlation between efficiency and pump surface modification should necessarily be expected. That is, regardless of the coefficient of static and dynamic friction between the rotor and journal or rotor and lower housing, the no-slip condition for the lubricant holds at the solid surfaces, and the frictional losses are viscous in nature.

The polyurethane coatings have contributed significantly to the antithrombogenicity of the pump. Specifically, the application of polyurethane material 18 to the cannulae/housing interface has had striking results: no clots have been found in any of the five studies at this juncture, nor have they been found in 39 other accumulated implantation studies. This has been a major improvement of the present pump device 10 based on prior studies (Goldstein, A. H., Pacella, J. J., Trumble, D. R., et al.: Development of an implantable centrifugal blood pump. *ASAIO Trans* 38:M362–M365, 1992). In addition, the polyurethane coating of the seal and the use of pyrolytic carbon impeller blades have been associated with decreased thrombus formation, as shown in comparisons of the first study of 14 days duration and all four subsequent studies (10, 28, 35, and 154-day lengths).

The prevention of thoracic cavity fluid leakage into the electronic components of the pump stator 34 through various environmental sealing techniques has been of utmost importance. Developed methods involve coating the stator windings in polyurethane and increasing the size of the stator mold to allow thicker epoxy coverage. As a result, the occurrence of fluid-based corrosion has been significantly reduced. No evidence of motor failure was found in the 35-day study; however, the 154-day study was ended due to corrosion of the stator by chest fluid. In this study, the time to catastrophic motor failure secondary to corrosion was increased significantly from the 28-day study.

The use of anticoagulation administered in all experiments following the first 14-day study appears to have contributed to a significant reduction in pump thrombosis. However, the role of specific anticoagulant drugs as anti-thrombotic agents in sheep will be addressed separately.

The change from 0.9% saline lubricant to sterile water in the 154-day study on POD 86 was made based on the findings from the 35-day experiment. This change appears to have reduced the occurrence of salt deposition within the occlusion system as indicated by decreased variation in the perfusion system pressures and flows and more reliable delivery of lubricant to the pump.

Thus, with the present pump device, modifications in blood surface materials, blood surface coatings, and electronic component fabrication and environmental sealing have had a positive impact on pump performance as indicated by increased survival times, decreased pump clot formation, less pump component wear, lower pump stator surface temperatures, and increased in fluid corrosion resistance. Moreover, both the expense and the learning curve associated with these long-term implantation studies have prompted changes from one study to the next. For example, in the 35-day study, salt thought to be was precipitating from saline solution due to low lubricant flow rates, blocking the lubricant conduit, and preventing lubricant from reaching the pump. Eventually, pump failure occurred. This knowledge was applied in an ongoing study of 154 days by substituting sterile water for saline. The result was increased reliability of pump lubricant delivery and elimination of episodes of flow blockage.

The myriad of device-centered modifications in these studies were made with the goals of achieving longer survival times, increasing pump reliability, and proving feasibility of the device as a VAD. As a result, the centrifugal pump has evolved through multiple intermediate forms, with increasing improvements in its performance.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A blood pump device comprising:
   a first portion having a chamber and an inlet and an outlet port in fluidic communication with the chamber through which blood can flow; and
   a second portion having a stator mechanism for rotating a rotor mechanism and powered by electricity and a rotor mechanism disposed adjacent to and rotated by the stator mechanism when the stator mechanism receives electricity, said second portion having a journal disposed about the rotor mechanism to provide support therewith, said second portion having an impeller disposed in the chamber, said impeller having a shaft, said second portion having a seal member for sealing about the shaft of the impeller, said seal member fixedly attached to said journal so that the seal member is supported by the journal, said shaft extending into the rotor mechanism and turns with the rotor mechanism as the rotor mechanism is turned by the stator mechanism.

2. A blood pump as described in claim 1 wherein the second portion includes adhesive material disposed between the seal member and the journal and wherein said rotor having a rotor post connected to the impeller shaft and having an end adjacent to the seal member, said end having rounded edges to prevent abutment against any adhesive material disposed between the seal member and the journal.

3. A device as described in claim 2 wherein the journal has a surface adjacent to the rotor which has been polished to a surface finish of less than or equal to 2.54 µm for enhanced durability.

4. A device as described in claim 3 wherein the rotor has an outer surface which has been polished to a surface finish of 2.54 µm.

5. A device as described in claim 4 wherein the seal member has an outer surface and wherein the second portion includes a coating surrounding and sealing the outer surface.

6. A device as described in claim 5 wherein the rotor comprises a rust-proof coating disposed on the outer surface.

7. A device as described in claim 6 wherein the seal member is one piece.

8. A device as described in claim 7 wherein the second portion includes a housing positioned about the journal, rotor mechanism and stator mechanism.

9. A blood pump device comprising:
   a first portion having a chamber and an inlet and outlet port in fluidic communication with the chamber through which blood can flow;
   a second portion having a stator mechanism for rotating a rotor mechanism and powered by electricity and a rotor mechanism disposed adjacent to and rotated by the stator mechanism when the stator mechanism receives electricity, said second portion having a journal disposed about the rotor mechanism to provide support therewith, said second portion having an impeller disposed in the chamber, said impeller having a shaft, said second portion having a seal member for sealing about the shaft of the impeller, said seal member fixedly attached to said journal so that the seal member is supported by the journal, said second portion having an infusion port for providing lubricant material about the rotor, said infusion port having an inner diameter greater than 0.05 inches for minimizing pressure needed to introduce lubricant material into the blood pump, said shaft extending into the rotor mechanism and turns with the rotor mechanism as the rotor mechanism is turned by the stator mechanism.

10. A device as described in claim 9 wherein the second portion includes a housing member in direct fluid communication with the infusion port and said second portion having a barbed tubing connector attached directly into the housing member of the second portion for connecting with a tube providing lubricant material.

11. A device as described in claim 10 wherein the infusion port is polished to a surface finish of less than 2.54 μm.

12. An improved blood pump device comprising:

a first portion having a chamber and an inlet and outlet port in fluidic communication with the chamber through which blood can flow; and a second portion having a stator mechanism for rotating a rotor mechanism and powered by electricity and a rotor mechanism disposed adjacent to and rotated by the stator mechanism when the stator mechanism receives electricity, said second portion having a journal disposed about the rotor mechanism to provide support therewith, said second portion having an impeller disposed in the chamber, said impeller having a shaft, said stator comprised of a thermally conductive epoxy material to efficiently transmit heat to surrounding tissues about the blood pump which is generated when the rotor mechanism rotates, said shaft extending into the rotor mechanism and turns with the rotor mechanism as the rotor mechanism is turned by the stator mechanism.

13. A device as described in claim 12 wherein the second portion comprises an environmentally sealed connector for attaching a power wire to the stator mechanism for receiving electricity.

14. A device as described in claim 13 wherein the stator has an outer surface and the second portion includes a coating sealing the outer surface.

* * * * *